US011820975B2

(12) United States Patent
Bani et al.

(10) Patent No.: US 11,820,975 B2
(45) Date of Patent: Nov. 21, 2023

(54) HUMAN BLOOD BRAIN BARRIER MODEL

(71) Applicant: National Research Council of Canada, Ottawa (CA)

(72) Inventors: Mahmud Bani, Ottawa (CA); Danica Stanimirovic, Ottawa (CA); Maria Ribecco-Lutkiewicz, Ottawa (CA)

(73) Assignee: National Research Council of Canada, Ottawa (CA)

( * ) Notice: Subject to any disclaimer, the term of this patent is extended or adjusted under 35 U.S.C. 154(b) by 98 days.

(21) Appl. No.: 15/533,250

(22) PCT Filed: Dec. 9, 2015

(86) PCT No.: PCT/CA2015/051297
§ 371 (c)(1),
(2) Date: Jun. 5, 2017

(87) PCT Pub. No.: WO2016/090486
PCT Pub. Date: Jun. 16, 2016

(65) Prior Publication Data
US 2017/0362584 A1    Dec. 21, 2017

Related U.S. Application Data

(60) Provisional application No. 62/089,512, filed on Dec. 9, 2014.

(51) Int. Cl.
C12N 11/02       (2006.01)
C12N 5/071       (2010.01)
C12Q 1/02        (2006.01)
C12N 5/073       (2010.01)

(52) U.S. Cl.
CPC .............. *C12N 11/02* (2013.01); *C12N 5/069* (2013.01); *C12N 5/0697* (2013.01); *C12Q 1/02* (2013.01); *C12N 5/0605* (2013.01); *C12N 2502/08* (2013.01); *C12N 2502/28* (2013.01); *C12N 2503/04* (2013.01); *C12N 2506/45* (2013.01)

(58) Field of Classification Search
None
See application file for complete search history.

(56) References Cited

FOREIGN PATENT DOCUMENTS

| WO | WO 2011/159572 | 12/2011 | |
|---|---|---|---|
| WO | WO-2011159572 A2 * | 12/2011 | ............. C12N 5/069 |
| WO | WO 2014/074695 | 5/2014 | |
| WO | WO-2014203087 A1 * | 12/2014 | ........... C12N 5/0618 |

OTHER PUBLICATIONS

Ketabi-Kiyanvash et al., Cell and Tissue Research, vol. 328, pp. 19-29 (2007).*

(Continued)

*Primary Examiner* — Sean C. Barron
(74) *Attorney, Agent, or Firm* — Wolf, Greenfield & Sacks, P.C.

(57) ABSTRACT

An in vitro population of human brain endothelial cells (hBECs) expressing claudin-5, occludin, ZO-1 and GLUT-1 and expressing one or more of FZD7, WNT7A, WNT7B, APCDD1, STRA6 and ZO-3 is provided. A blood brain barrier (BBB) comprising the hBECs and use of the BBB for analyzing permeability characteristics of a test agent are provided.

4 Claims, 16 Drawing Sheets

(56) References Cited

OTHER PUBLICATIONS

Mark et al., American Journal of Physiology: Heart and Circulatory Physiology, vol. 282, pp. H1485-H1494 (2002). (Year: 2002).*
Lippmann et al., Scientific Reports, vol. 4, No. 4160, pp. 1-10; electronically published Feb. 21, 2014. (Year: 2014).*
Ketabi-Kiyanvash et al., Cell and Tissue Research, vol. 328, pp. 19-29 (2007)(of record). (Year: 2007).*
Mark et al., American Journal of Physiology: Heart and Circulatory Physiology, vol. 282, pp. H1485-H1494 (2002) (of record). (Year: 2002).*
Bernas et al. Establishment of primary cultures of human brain microvascular endothelial cells to provide an in vitro cellular model of the blood-brain barrier. Nature Protocols vol. 5, pp. 1265-1272 (2010). (Year: 2010).*
Patabendige et al. A detailedmethodforpreparationofafunctionaland flexible blood-brain barriermodelusingporcine brain endothelialcells. Brain Res. Jul. 12, 2013;1521:16-30. (Year: 2013).*
Hatherell et al. Development of a three-dimensional, all-human in vitro model of the blood-brain barrier using mono-, co-, and tri-cultivation Transwell models. Journal of Neuroscience Methods (2011), 199(2), 223-229. (Year: 2011).*
PCT/CA2015/051297, dated Mar. 14, 2016, International Search Report and Written Opinion.
Haqqani et al., Multiplexed evaluation of serum and CSF pharmacokinetics of brain-targeting single-domain antibodies using a NanoLC-SRM-ILIS method. Mol Pharm. May 6, 2013;10(5):1542-56. doi: 10.1021/mp3004995. Epub Dec. 6, 2012.
Li et al., Generation of induced pluripotent stem cells from human amniotic fluid cells by reprogramming with two factors in feeder-free conditions. J Reprod Dev. 2013;59(1):72-7. Epub Nov. 9, 2012.
Li et al., Pluripotency can be rapidly and efficiently induced in human amniotic fluid-derived cells. Hum Mol Genet. Nov. 15, 2009;18(22):4340-9. doi:10.1093/hmg/ddp386. Epub Aug. 13, 2009.
Lippmann et al., Derivation of blood-brain barrier endothelial cells from human pluripotent stem cells. Nat Biotechnol. Aug. 2012;30(8):783-91.
Ng et al., A protocol describing the use of a recombinant protein-based, animal product-free medium (APEL) for human embryonic stem cell differentiation as spin embryoid bodies. Nat Protoc. 2008;3(5):768-76. doi: 10.1038/nprot.2008.42.
Stanimirovic et al., Blood-brain barrier models: in vitro to in vivo translation in preclinical development of CNS-targeting biotherapeutics. Expert Opin Drug Discov. Feb. 2015;10(2):141-55. doi: 10.1517/17460441.2015.974545. Epub Nov. 12, 2014.
Weksler et al., The hCMEC/D3 cell line as a model of the human blood brain barrier. Fluids Barriers CNS. Mar. 26, 2013;10(1):16. doi:10.1186/2045-8118-10-16.
Yang et al., Human cardiovascular progenitor cells develop from a KDR+ embryonic-stem-cell-derived population. Nature. May 22, 2008;453(7194):524-8. doi: 10.1038/nature06894. Epub Apr. 23, 2008.

* cited by examiner

HUMAN BLOOD BRAIN BARRIER MODEL

CROSS REFERENCE TO PRIOR APPLICATIONS

This application is a national stage filing under 35 U.S.C. § 371 of International Application No. PCT/CA2015/051297, filed Dec. 9, 2015, which claims priority under the Paris Convention and benefit under 35 U.S.C. § 119(e) to U.S. Provisional Patent Application 62/089,512, filed Dec. 9, 2014, which is incorporated herein by reference as if set forth in its entirety.

FIELD OF THE DESCRIPTION

The present description relates generally to human blood brain barrier (BBB) models. More specifically, the present description relates to a human BBB model comprising brain endothelial cells (BECs) derived from amniotic fluid cells and the model's use in screening prospective BBB-permeant compounds.

BACKGROUND OF THE DESCRIPTION

The blood vessels in the brain form a blood brain barrier (BBB), which limits the flow of molecules and ions from the blood into neural tissues. The BBB maintains homeostasis in the brain and protects the central nervous system from toxins and pathogens. Dysfunction of the BBB is implicated in various neurological diseases. Brain endothelial cells (BECs), which form the BBB, are highly polarized cells held together by tight junctions that limit the flow of molecules and ions across paracellular space.

Most in vitro BBB models comprise of primary or immortalized cells from non-human sources, such as, rat, mouse, porcine, bovine or cynomolgus monkey. Human in vitro BBB models are desirable, at least due to species differences in genes and proteins involved with the BBB and in view of the recent development of biologic drugs some of which have species selectivity against BBB receptors.

Primary BECs have been isolated from autopsy tissues and from patients with epilepsy or brain tumors. However, primary human BECs have rarely been used in in vitro human BBB models for drug transport evaluation due to one or more of: low cell yields, difficulties in accessing patient samples, patient-related heterogeneity, fast de-differentiation, and poor trans-endothelial electrical resistance (TEER; a measure to evaluate the integrity of the blood brain barrier).

A limited number of immortalized human BEC lines have been developed using immortalization protocols involving SV-40 large-T antigen. The best characterized human BEC line is hCMEC/D3. Use of hCMEC/D3 as an in vitro BBB model was reviewed by Weksler et al. (2013). A comparative study of BBB marker expression, barrier tightness and paracellular permeability among four immortalized human BEC lines (hBMEC, hCMEC/D3, TY10, and BB19) demonstrated that low TEER values (below 45 $\Omega \cdot cm^2$) observed in each cell line could not be improved. These immortalized BEC lines often diverge significantly, geno- and/or phenotypically, from primary cells. For example, genes related to the immortalization procedure, implicated in RNA processing, DNA repair, immune response, and mitosis were found to be significantly up-regulated in the hCMEC/D3 cell line relative to primary human BECs (Eigenmann et al., 2013, Fluids and Barriers of the CNS, 10: 33, 1-16).

More recently, human stem cell and/or progenitor cell sources have been used to derive BECs. Unlike primary BEC cultures, stem cells offer a theoretically unlimited expansion capacity. Human embryonic stem cells (ESCs) and human induced pluripotent stem cells (iPSCs) have been used to generate functional BECs expressing various BBB tight junction proteins, transporters, and receptors (Lippmann et al., 2012, Human Blood-Brain Barrier Endothelial Cells Derived from Pluripotent Stem Cells, Nat Biotechnol. 2012 August; 30(8): 783-791. doi: 10.1038/nbt.2247, PMCID: PMC3467331; Wilson et al., 2015, Exploring the effects of cell seeding density on the differentiation of human pluripotent stem cells to brain microvascular endothelial cells, Fluids Barriers CNS. 2015; 12: 13. doi: 10.1186/s12987-015-0007-9, PMCID: PMC4455681. Lippmann et al., 2014, A retinoic acid-enhanced, multicellular human blood-brain barrier model derived from stem cell sources, Sci Rep. 2014; 4: 4160. Published online 2014 Feb. 24. doi: 10.1038/srep04160, PMCID: PMC3932448).

The BBB phenotype of these stem-cell derived BECs was enhanced by adding retinoic acid (RA), which induced an earlier onset of VE-cadherin expression, higher tight junction complexity, and mRNA up-regulation of multiple efflux pumps (Lippmann et al., 2012, Human Blood-Brain Barrier Endothelial Cells Derived from Pluripotent Stem Cells, Nat Biotechnol. 2012 August; 30(8): 783-791. doi: 10.1038/nbt.2247, PMCID: PMC3467331; Wilson et al., 2015, Exploring the effects of cell seeding density on the differentiation of human pluripotent stem cells to brain microvascular endothelial cells, Fluids Barriers CNS. 2015; 12: 13. Published online 2015 May 21. doi: 10.1186/s12987-015-0007-9, PMCID: PMC4455681. Lippmann et al., 2014, A retinoic acid-enhanced, multicellular human blood-brain barrier model derived from stem cell sources, Sci Rep. 2014; 4: 4160. doi: 10.1038/srep04160, PMCID: PMC3932448). A combination of RA treatment and sequential co-culture of fibroblast-iPSC-derived BECs with human pericytes followed by astrocytes and neurons differentiated from neural progenitors elevated TEER levels to over 5000 $\Omega \cdot cm^2$ (Lippmann et al., 2012, Human Blood-Brain Barrier Endothelial Cells Derived from Pluripotent Stem Cells, Nat Biotechnol. 2012 August; 30(8): 783-791. doi: 10.1038/nbt.2247, PMCID: PMC3467331; Wilson et al., 2015, Exploring the effects of cell seeding density on the differentiation of human pluripotent stem cells to brain microvascular endothelial cells, Fluids Barriers CNS. 2015; 12: 13. doi: 10.1186/s12987-015-0007-9, PMCID: PMC4455681. Lippmann et al., 2014, A retinoic acid-enhanced, multicellular human blood-brain barrier model derived from stem cell sources, Sci Rep. 2014; 4: 4160. doi: 10.1038/srep04160, PMCID: PMC3932448).

Other attempts to develop human BBB model from stem cell sources have been reported.

For example, human cord blood-derived hematopoietic stem cells were differentiated to endothelial cells, using Endothelium Growth Medium-2 (EGM-2; Lonza) and co-cultures of bovine pericytes to derive 'brain-like endothelial cells (BLEC) (Cecchelli et al., 2014 PLOS ONE 9(6) e99733). Further co-culturing BLECs with pericytes from non-human species facilitated maturation of BECs towards a BBB phenotype, as evidenced by expression of influx transporters (SLC7A5, SLC16A1), glucose transporters (GLUT-1 or SLC2A1), several ATP-binding cassette (ABC) transporters, and other BBB-specific receptors. BLECs exhibited low TEER values (70 $\Omega \cdot cm^2$ and 170 $\Omega \cdot cm^2$) in mono- and co-cultures, respectively. This model requires sorting cells by FACS, using six different cell surface markers, which is quite challenging from one sample to another. There is no evidence of long term cryopreservation and passages with the same functionality. Furthermore, pericytes and/or astrocytes from non-human sources are required for this model to function as an in vitro BBB system.

Human cord blood circulatory endothelial progenitor cell (EPC)-derived endothelial cells were grown in EGM-2 and co-cultured with rat astrocytes to achieve ECs exhibiting expression of ZO-1, occludin, claudin 5, CD31, VE-cadherin, GLUT1, and P-glycoprotein (Boyer-Di Ponio et al., 2014, PLOS ONE 9, e84179). These BECs were tested for the permeability of some hydrophilic solutes. However, this model is not renewable, because it uses progenitors (not stem cells). In addition, its functionality, although limited, depends on rat astrocytes (i.e., another cell type from a non-human cell source). Finally, the model has not been well-characterized and it remains to be tested for small molecules and biologics.

It is desirable to obviate or mitigate one or more of the above deficiencies.

SUMMARY OF THE DESCRIPTION

In a first aspect, an in vitro population of human brain endothelial cells (hBECs), the hBECs expressing claudin-5, occludin, ZO-1 and GLUT-1 and expressing one or more of FZD7, WNT7A, WNT7B, APCDD1, STRA6 and ZO-3.

In one embodiment of the first aspect, the hBECs express FZD7, WNT7A, WNT7B, APCDD1, STRA6 and ZO-3. In one embodiment of the first aspect, the hBECs express ABCG2, PGP and transferrin receptor. In one embodiment of the first aspect, the hBECs express a TEER between about 400 and 700 $\Omega \cdot cm^2$ when the hBECs are grown in a monolayer.

In one embodiment of the first aspect, the hBECs are cultured in the absence of one or more of conditioned medium, co-culture cells, hydrocortisone and retinoic acid.

In one embodiment of the first aspect, the hBECs are generated from induced pluripotent stem cells (iPSCs) and wherein the iPSCs are generated from human amniotic fluid (AF) cells.

In one embodiment of the first aspect, the cells are gown to confluence on a support, thereby obtaining a blood brain barrier.

In a second aspect, a method of generating human brain endothelial cells (hBECs) is provided. The method comprises: providing amniotic fluid (AF) cells; reprogramming the AF cells into induced pluripotent stem cells (iPSCs), thereby generating AF-iPSCs; differentiating the AF-iPSCs into hBECs, the hBECs expressing claudin-5, occludin, ZO-1 and GLUT-1 and expressing one or more of FZD7, WNT7A, WNT7B, APCDD1, STRA6 and ZO-3; and expanding the hBECs.

In one embodiment of the second aspect, the hBECs express FZD7, WNT7A, WNT7B, APCDD1, STRA6 and ZO-3. In one embodiment of the second aspect, the hBECs express ABCG2, PGP and transferrin receptor.

In one embodiment of the second aspect, the expanding comprises growing the hBECs into a confluent monolayer, the hBECs in the confluent monolayer expressing a TEER between about 400 and 700 $\Omega \cdot cm^2$.

In one embodiment of the second aspect, the hBECs are differentiated and/or expanded in the absence of one or more of conditioned medium, co-culture cells, hydrocortisone and retinoic acid.

In a third aspect, a blood brain barrier (BBB) model is provided. The BBB model comprises: a permeable support having a surface comprising extracellular matrix proteins; and a plurality of human brain endothelial cells (hBECs), the plurality of hBECs expressing claudin-occludin, ZO-1 and GLUT-1 and expressing one or more of FZD7, WNT7A, WNT7B, APCDD1, STRA6 and ZO-3, the hBECs being grown to confluence on the permeable support.

In one embodiment of the third aspect, the plurality of hBECs express FZD7, WNT7A, WNT7B, APCDD1, STRA6 and ZO-3. In one embodiment of the third aspect, the plurality of hBECs express ABCG2, PGP and transferrin receptor.

In one embodiment of the third aspect, the plurality of hBECs express a TEER between about 400 and 700 $\Omega \cdot cm^2$.

In one embodiment of the third aspect, the plurality of hBECs grown to confluence on the permeable support are provided within a liquid-containing vessel, thereby forming a barrier between a top and bottom chamber of the vessel.

In one embodiment of the third aspect, the BBB further comprises one or more target cells, the target cells being provided in the bottom chamber of the vessel. In one embodiment of the third aspect, the one or more target cells are one or more of neurons, astrocytes or oligodendrocytes. In one embodiment of the third aspect, the plurality of hBECs and the one or more target cells are isogenic. In one embodiment of the third aspect, the one or more target cells comprise a reporter system.

In a fourth aspect, a method of analyzing blood-brain barrier permeability characteristics of a test agent is provided. The method comprises: providing the blood brain barrier model; contacting the blood brain barrier model with a test agent; and measuring permeability of the test agent with respect to the blood brain barrier model.

In one embodiment of the fourth aspect, the measuring comprises determining an amount of the test agent contacted with the blood brain barrier model and an amount of the test agent that permeated the blood brain barrier model.

In one embodiment of the fourth aspect, the measuring comprises determining the amount of the test agent that permeates the blood brain barrier model using a mass spectrometry-based method and/or an antibody-based method. In one embodiment of the fourth aspect, the mass spectrometry-based method is liquid chromatography-mass spectrometry (LC-MS), high performance liquid chromatography (HPLC) or liquid chromatography-mass spectrometry multiple reaction monitoring (LC-MRM). In one embodiment of the fourth aspect, the antibody-based method is enzyme-linked immunosorbent assay (ELISA) or LC-MRM. In one embodiment of the fourth aspect, the test agent is labelled and wherein the measuring comprises measuring an amount of the label as a surrogate for measuring the amount of the test agent. In one embodiment of the fourth aspect, the label is one of a radioactive label or a fluorescent label.

In one embodiment of the fourth aspect, the measuring the permeability of the test agent comprises measuring paracellular diffusion, membrane diffusion, carrier-mediated transport or receptor-mediated transcytosis of the test agent with respect to the blood brain barrier model.

In one embodiment of the fourth aspect, the blood brain barrier model further comprises a step of: measuring one or more effects of the test agent on the one or more target cells. In one embodiment of the fourth aspect, the measuring of one or more effects of the test agent comprises measurement of one or more of cell viability and cell function. In one embodiment of the fourth aspect, the integrity of the blood brain barrier model is assessed visually. In one embodiment of the fourth aspect, the test agent is a synthetic or biologic molecule that is small or large.

In a fifth aspect, a method of assessing blood brain barrier integrity is provided. The method comprises: providing a blood brain barrier; marking cells of the blood brain barrier to visually distinguish live and dead cells, and cell membranes; visually assessing confluence of the cells of the blood brain barrier; and determining the blood brain barrier is sufficiently tight to form a barrier if the visually assessed barrier lacks gaps equal to or larger than the diameter of brain endothelial cells between the cells; or determining the blood brain barrier is not sufficiently tight to form a barrier if the visually assessed barrier comprises one or more gaps equal to or larger than the diameter of brain endothelial cells between the cells.

In one embodiment of the fifth aspect, the visual assessing comprises obtaining an image of the marked cells of the blood brain barrier and assessing the image.

BRIEF DESCRIPTION OF THE DRAWINGS

The features of the invention will become more apparent in the following detailed description in which reference is made to the appended drawings wherein:

FIG. 1A depicts staining of control amniotic fluid cells (left column, control) and AF-iPSCs (middle column) with alkaline phosphatase (AP). The pluripotency of AF-iPSCs was also assessed by live TRA-1-81 staining (right column). FIG. 1B depicts expression of pluripotent stem cell markers in AF-iPSCs vs. control amniotic fluid cells obtained at 26 weeks gestation (AF26) by western blot analysis. The expression of OCT4, SOX2 and NANOG was several fold higher in AF-iPSCs compared with control AF cells (AF-26). FIG. 1C shows the expression of OCT4, NANOG, SOX2 and KLF4 in AF-iPSCs by immunostaining. FIG. 1D further depicts the expression of stem cell markers by double-staining with TRA-1-81 and OCT4 (top panel). F-Actin and CD30 were also used in combination with OCT4 nuclear localization in AF-iPSCs.

FIG. 2A depicts karyotype analysis of amniotic fluid cells (AF; top) and an AF-iPSC clone (bottom). FIG. 2B depicts DNA methylation analysis of NANOG and OCT4 in AF cells (top) and an AF-iPSC clone (bottom).

FIG. 3A illustrates the expression of several BBB related genes in hAF-iPSC-BECs vs. HBMECs using RT-PCR.

FIGS. 3B-D show further characterization of AF-iPSCs vs. control AF cells (AF26) and HBMECs with BBB markers by staining (B, C right panel and D) and Western blot (C left bottom panel).

FIG. 5A illustrates formation of capillary-like structures for AF-iPSC-BECs grown on Matrigel. FIG. 5B shows similar structures formed by AF-iPSC-BBECs on PGA. Cells have been stained with CFDA (a cell survival marker).

FIG. 6A depicts in vitro BBB transwell system. FIG. 6B depicts a live-stained BBB monolayer on an insert, staining done with CFDA and CMO fluorescent dyes, per the BBB View method provided herein. FIG. 6C depicts sodium fluorescein permeability in AF-iPSC-BECs vs. HBMECs. FIG. 6D depicts the correlation between TEER values and sucrose Pe for AF-iPSC-BECs (N=11). FIG. 6E shows the correlation between TEER value and BBB integrity, as determined visually by BBB View.

FIG. 7A shows TEER values of a BBB model comprising AF-iPSC-BECs cultured in astrocyte conditioned media (ACMx2) for 24 hours. FIG. 7B shows TEER values of a BBB model comprising AF-iPSC-BECs cultured in the presence of hydrocortisone (HC).

FIG. 8A depicts expression of receptor-mediated transcytosis (RMT) receptors, transferrin receptor (TfR) and insulin growth factor-1 receptor (IGF1R) in AF-iPSC-BEC by RT-PCR and immunochemistry. FIG. 8B depicts internalization of antibodies recognizing RMT receptors into AF-iPSC-BECs (receptor-mediated endocytosis). FIG. 8C depicts a flowchart summarizing use of the in vitro BBB model to assess the ability of various $V_H$Hs to cross the BBB. FIG. 8D depicts $P_{app}$ values of three co-administered antibodies FC5Fc, A20.1 and EG2. FC5Fc compared to negative controls (results are average $P_{app}$ values obtained in 5-6 independent experiments). FIG. 8E depicts levels of IGF1R-3, IGF1R-4, and Fc-IGF1R5 in the bottom chamber of a Transwell assay at different time points.

FIG. 10A depicts differentiation of astrocytes (labeled with glial fibrillary acidic protein, GFAP), oligodendrocytes (labeled with myelin basic protein, MBP) and neurons from AF-iPSCs. FIG. 10B shows that the neural progenitors generated from AF-iPSCs are OCT4 negative (not iPSC anymore), while they express SOX2, NESTIN and PAX6. FIG. 10C depicts a Western blot confirming high levels of PAX6 in AF-iPSC-derived neural progenitors (iPS-NPA) compared with those of control AF cells (26 weeks of gestation) and AF-iPSCs. FIG. 10D shows that AF-iPSC-derived neural progenitors form OCT4 negative, SOX2 and PAX6 positive neural rosettes. FIG. 10E confirms that AF-iPSCs can also form OCT4 negative, SOX2 positive NESTIN positive neurospheres. FIG. 10F illustrates neural rosette morphology. FIG. 10G depicts a Western blot confirming high levels of SOX2 and NESTIN in AF-iPSC-derived neurospheres.

FIG. 11A depicts immunocytochemical characterization of AF-iPSC-derived neurons, using a wide range of neuronal markers. FIG. 11B depicts a Western blot confirming the expression of NeuN and MAP2 in AF-iPSC-derived neuronal cells (iPS-NC) vs. control amniotic fluid cells (AF26) and AF-iPS cells. Mouse cortex was used as a positive control. FIG. 11C shows voltage-clamp recording from an iPSC-derived neuron. FIG. 11D depicts AF-iPSCderived neurons showing tetrodotoxin (TTX)-sensitive spiking activity, using the whole-cell patch-clamp technique. FIG. 11E depicts voltage response to a series of current pulses: current-voltage relationship at 500 ms (open circles) and 800 ms (filled circles) after onset of current pulses. Application of 1 µM TTX eliminated spiking activity.

FIGS. 12A-L depict aspects of the application of AF-iPSC-BECs in drug development. The upper panel of FIG. 12 is a diagram representing applications an AF-iPSC-BECs transwell BBB model to assess the permeability of drug candidates and the isogenic AF-iPSC-derived neurons (and/or other cell types) as their target. FIGS. 12A-L show neurotoxicity assays, using isogenic AF-iPSC-derived neurons. FIGS. 12A-F depict neuronal viability determined by CFDA staining (green) in the absence (FIGS. 12A-C) or presence (FIGS. 12D-F) of glutamate for 6 hours in culture.

Figure 1:
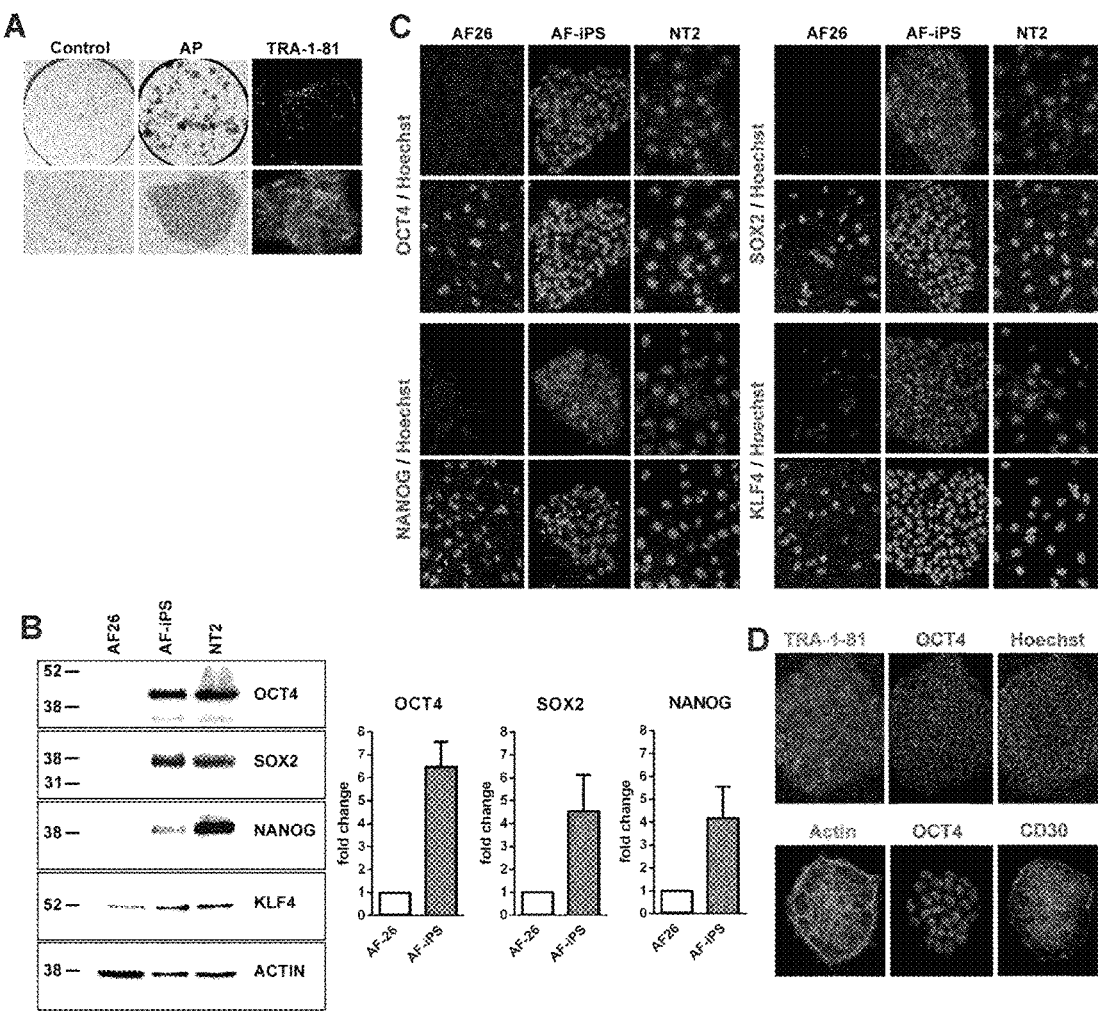
FIGS. 1A-D illustrate characterization of induced pluripotent stem cells (iPSCs) from human amniotic fluid cells (i.e., AF-iPSCs).

Additional aspects and advantages of the present invention will be apparent in view of the following description. The detailed descriptions and examples, while indicating preferred embodiments of the invention, are given by way of illustration only, as various changes and modifications within the scope of the invention will become apparent to those skilled in the art in light of the teachings of this invention.

DETAILED DESCRIPTION OF THE NON-LIMITING EXEMPLARY EMBODIMENTS

Unless defined otherwise, all technical and scientific terms used herein generally have the same meaning as commonly understood by one of ordinary skill in the art to which this invention belongs.

General Description of the Blood Brain Barrier Model

Most BBB models include chemical mediators, such as retinoic acid, and/or co-culture of brain endothelial cells (BECs; primary cells or BECs derived from cord blood or fibroblast-iPSCs) with brain astrocytes, pericytes and/or neurons, the co-culture cells being rat, bovine or human cells that are primary cells or cells derived from embryonic neural progenitor cells.

The present disclosure is based on the inventors' discovery that iPSCs derived from human amniotic fluid cells (AF-iPSCs) can be differentiated into brain endothelial cells (AF-iPSC-BECs), comprising one or more different characteristics relative to primary BECs and BECs derived from other pluripotent sources (e.g., embryonic sources, cord blood, iPSCs derived from fibroblasts) and immortalized BEC lines. The BBB model provided herein comprises permeability properties that are equal to and/or better than other in vitro BBB models, even in the absence of one or more of co-culture cells and chemical inducers.

Human Brain Endothelial Cell (hBEC) Population

In one embodiment, the BECs provided herein express markers of brain endothelial cells, including claudin-5, occludin, ZO-1 and GLUT-1. In one embodiment, the BECs provided herein express one or more of the following brain endothelial markers: ABCG2, PGP and transferrin receptor.

In contrast to other BECs, the BECs provided herein exhibit a Wnt gene expression pattern that differs from other BECs. For example, the BECs provided herein express one or more of FZD7, WNT7A, WNT7B and APCDD1. Expression of genes in the Wnt pathway is relevant to BECs at least because Wnt/beta-catenin signaling is required for brain microvasculature angiogenesis and at least some aspects of BBB formation (Daneman et al. Wnt/β-catenin signaling is required for CNS, but not non-CNS, angiogenesis. PNAS, 106(2): 641-646 doi:10.1073/pnas.0805165106).

FZD7 refers to frizzled class receptor 7, which is also known as FzE3. This gene represents a member of the 'frizzled' gene family. The FZD7 protein contains an N-terminal signal sequence, 10 cysteine residues typical of the cysteine-rich extracellular domain of Fz family members, 7 putative transmembrane domains, and an intracellular C-terminal tail with a PDZ domain-binding motif. FZD7 gene expression may downregulate APC function and enhance beta-catenin-mediated signals in poorly differentiated human esophageal carcinomas.

WNT7A refers to wingless-type MMTV integration site family, member 7A. This gene is a member of the WNT gene family, which consists of structurally related genes that encode secreted signaling proteins. These proteins have been implicated in oncogenesis and in several developmental processes, including regulation of cell fate and patterning during embryogenesis. This gene is involved in the development of the anterior-posterior axis in the female reproductive tract, and also plays a critical role in uterine smooth muscle pattering and maintenance of adult uterine function. Mutations in this gene are associated with Fuhrmann and Al-Awadi/Raas-Rothschild/Schinzel phocomelia syndromes.

WNT7B refers to wingless-type MMTV integration site family, member 7B. Among members of the human WNT family, this gene product is most similar to WNT7A protein.

APCDD1 refers to adenomatosis polyposis coli downregulated 1, which is also known as HHS; HTS; B7323; HYPT1; DRAPC1; FP7019. This locus encodes an inhibitor of the Wnt signaling pathway. Mutations at this locus have been associated with hereditary hypotrichosis simplex. Increased expression of this gene may also be associated with colorectal carcinogenesis.

In one embodiment, in contrast to other BECs, the BECs provided herein exhibit a the membrane transporter STRA6 and/or the tight junction protein ZO-3, both of which are relevant to a functional BBB.

STRA6, refers to stimulated by retinoic acid 6, which is also known as MCOPS9, MCOPCB8, PP14296. The protein encoded by this gene is a membrane protein involved in the metabolism of retinol. The encoded protein acts as a receptor for retinol/retinol binding protein complexes. This protein removes the retinol from the complex and transports it across the cell membrane. Defects in this gene are a cause of syndromic microphthalmia type 9 (MCOPS9). Several transcript variants encoding a few different isoforms have been found for this gene.

ZO-3 refers to zona occuldens protein 3. The protein encoded by this gene is a member of a family of tight junction associated proteins that function as cross-linkers, anchoring the TJ strand proteins to the actin-based cytoskeleton. The protein contains three PDZ (postsynaptic density, disc-large, ZO-1) domains, a single SH3 (Src Homology-3) domain and a GK (guanylate kinase) domain, the presence of which identifies them as members of the membrane-associated guanylate kinase (MAGUK) protein family. The protein also has an acidic domain at the C-terminal region of the molecule not found in other MAGUK proteins. It has been demonstrated that the first PDZ domain is involved in binding the C-terminal —Y—V motif of claudins.

In one embodiment, the hBECs provided herein, when grown in a monolayer, exhibit a TEER of about 400-1200

Ω·cm². The TEER value is a measurement indicative of impermeability of an endothelial cell monolayer to ion diffusion. In one embodiment, the hBECs provided herein, when grown in a monolayer, exhibit a TEER of about 400-700 Ω·cm².

In one embodiment, the TEER value of a monolayer of the provided BECs may be obtained by culturing the provided BECs in the absence of one or more of conditioned medium, co-culture cells, hydrocortisone and retinoic acid.

In one embodiment, the TEER value of a monolayer of the provided BECs may be increased by culturing the provided BECs in the presence of one or more of conditioned medium, co-culture cells, hydrocortisone and retinoic acid.

Human Brain Endothelial Cells generated from Amniotic Fluid-Derived Induced Pluripotent Stem Cells (AF-iPSC-BECs)

In one aspect, the hBECs provided herein are generated from induced pluripotent stem cells (iPSCs), the iPSCs being generated from amniotic fluid cells (AF-iPSCs). BECs generated from AF-iPSCs are referred to herein as AF-iPSC-BECs.

Human amniotic fluid cells (AF cells, or AFCs) are routinely obtained by amniocentesis. Accordingly, AFCs are not subject to the ethical concerns associated with ESCs. AFCs can be obtained from a specific donor, and preserved for use at a later time during the donor's life, thereby providing a means for personalized medicine. To date, fewer immunogenicity issues have been identified in AFCs relative to other stem cell sources (Sun et al., 2015, Scientific Reports 5, Article number: 11560, doi:10.1038/srep11560; Li et al., 2015 PLoS One. 2015; 10(4): e0123350. doi: 10.1371/journal.pone.0123350; Roubelakis et al., 2013, PLoS One. 2013; 8(1): e54747, doi: 10.1371/journal.pone.0054747).

Twenty five amniotic fluid samples were obtained by the inventors with the approval from the relevant research ethics boards. Cultures of amniotic fluid cells were prepared in conventional and xeno-free media. AF-iPSCs were generated by electroporating parental AFCs with POU5F1 (OCT4), SOX2, CMYC, KLF4 and NANOG. More than 500 AF-iPSC colonies were obtained, from which 10 clones were further established and 2 clones were applied to comprehensive cellular and molecular analyses and finalized based on their genetic stability, reduced methylation state and consistent expression of pluripotent stem cell markers for over 20 passages in culture.

AF-iPSC clones maintained normal karyotypes and endogenous expression of OCT4, SOX2, KLF4, NANOG and TRA-1-81 over several passages. The epigenetic state of the AF-iPSCs was assessed by observing significant reduction in DNA methylation in the OCT4 and NANOG promoter regions, confirming a fully reprogrammed state. AF-iPSC clones were differentiated into endodermal (i.e., BEC; Example 2), ectodermal (i.e., neurons, astrocytes and oligodendrocytes) and mesodermal (i.e., beating cardiac myocytes and erythroblasts; data not shown) cell lineages.

In one embodiment, the AF-iPSC-BECs provided herein may be obtained and cultured in the absence of one or more of: i) conditioned medium; ii) co-culture cells; and iii) chemical inducers, such as, for example, hydrocortisone or retinoic acid. AF-iPSC-BECs obtained and/or cultured in the absence of such components comprise one or more of the characteristics described herein, such as, doubling time, Wnt pathway gene expression pattern, TEER value, and cell marker(s).

In one embodiment, the AF-iPSC-BECs may be selected using VE-cadherin.

BBB Model Comprising the AF-iPSC-Derived BECs:

In one aspect, a BBB model comprising the AF-iPSC-BECs provided herein is provided. The BBB model comprises: i) a population of hAF-iPSC-BECs, as described above, on ii) a permeable support, the permeable support comprising extracellular matrix proteins.

In one embodiment, hAF-iPSC-BECs seeded on the permeable support may be provided in a container comprising a liquid, such that the seeded monolayer forms a barrier between a top and a bottom chamber of the container. For example, hAF-iPSC-BECs may be seeded on a Transwell insert, which may be placed in one well of a multi-well plate under conditions suitable for monolayer formation and cell growth. For example, AF-iPSC-derived BECs may be seeded at density of about 500,000 cells/insert and may be maintained in EM medium during TEER measurement.

In one embodiment, the hAF-iPSC-BECs monolayer is suitable for use in a BBB model when the cells are confluent and express a TEER of about 300-1200 Ω·cm², preferably a TEER of at least about 400 Ω·cm².

In one embodiment, the BBB model comprises hAF-iPSC-BECs in the absence of co-culture cells.

In one embodiment, co-culture cells such as, for example, neural progenitor cells, neurons or astrocytes, may be included in the BBB model provided herein. In one preferred embodiment, co culture cells may be derived from the AF-iPSCs provided herein. For examples, AF-iPSC-derived BECs were co-cultured with either isogenic or commercially-available human astrocytes, using non-contact or contact models. In other examples, cells were co-cultured with human pericytes.

In one embodiment, one or more target cells may be provided in a bottom chamber of the container. For example, one or more neural cell type, such as neurons or astrocytes (e.g., neurons or astrocytes derived from AF-iPSCs) may be provided in the bottom chamber of the container). By target cells, we mean cells that are the target of a test agent, as described further below.

In one preferred embodiment, the BBB comprises isogenic cells. In one particularly
preferred embodiment, BBB cells, co-culture cells and/or target cells are isogenic.

In one particularly preferred embodiment, the target cells comprise a reporter system. Suitable reporter systems are known in the art.

In one embodiment, integrity of the BBB on the support may be visually assessed, as described further herein below.

Use of the BBB Model to Test an Agent's Capacity to Cross a BBB

In one aspect, the BBB model provided herein is used to assess a test agent's capacity to permeate the BBB. Test agents suitable for testing with the BBB model provided herein include, but are not limited to, synthetic or biologic molecules, small or large molecules, toxins or microorganisms. For example, dopamine, sucrose, Na Fluorescein, diazepam, cyclosporine, glutamate, etc.

In one embodiment, a method of analyzing blood-brain barrier permeability characteristics of a test agent is provided. The method comprises providing the blood brain barrier model provided herein; contacting the blood brain barrier with a test agent; and measuring the permeability of the test agent with respect to the blood brain barrier model. In one embodiment, measuring permeability of the test agent comprises determining an amount of the test agent contacted with the blood brain barrier model and an amount of the test agent that permeated the blood brain barrier model.

For example, a BBB model comprising hAF-iPSC-BECs may be seeded on a permeable support, such as, for example, in a Transwell™ system. Seeded BECs are then contacted with a test agent, for example, in a top chamber of a container in the Transwell system. One or more permeability characteristics of the test agent may then be measured. For example, the rate of test agent transport may be measured using radioactively-labelled sucrose, dopamine, cyclosporine or diazepam after a time period (e.g., 30, 60, 90 or 120 minutes) (Farrington et al., 2014, A novel platform for engineering blood-brain barrier-crossing bispecific biologics, FASEB J. 2014 November; 28(11):4764-78. doi: 10.1096/fj.14-253369; Stanimirovic et al., 2014, Blood-brain barrier models: in vitro to in vivo translation in preclinical development of CNS-targeting biotherapeutics. Expert Opin Drug Discov. 2015 February; 10(2):141-doi: 10.1517/17460441.2015.974545).

Further example of measuring permeability of the test agent using the BBB model provided herein include: determining the amount of the test agent that permeated the blood brain barrier model using a mass spectrometry-based method and/or an antibody-based method. For example, the mass spectrometry-based method may be LC-MS, HPLC or LC-MRM and the antibody-based method may be ELISA or LC-MRM.

As described above, the test agent may be labelled with a label, such that measuring permeability of the test agent using the BBB model provided herein comprises measuring an amount of the label as a surrogate for measuring the amount of the test agent. For example, the label may be one of a radioactive label or a fluorescent label.

In various embodiments, the BBB model provided herein is suitable for measuring measuring paracellular diffusion, membrane diffusion, carrier-mediated transport or receptor-mediated transcytosis of a test agent with respect to the blood brain barrier model.

Paracellular diffusion refers to movement of an agent in-between cells. Such movement may be prevented by tight junctions formed between BECs in a BBB. However, in some instances, small (e.g., <500 D) hydrophilic molecules may be capable of paracellular diffusion through a BBB.

Membrane diffusion may occur if lipophilic molecules dissolve in membrane lipids, such as, for example, diazepam, as illustrated in the Examples.

Carrier-mediated transport of an agent across a BBB is possible and testable using the BBB model provided herein. For example, active transport of small molecules such as glucose by specific transporter such as Glut-1, may occur in a BBB.

Receptor-mediated transcytosis of an agent across a BBB is possible and testable using the BBB model provided herein. Receptor-mediated transcytosis refers to active transport of large molecules through BECs and involves engagement of receptor triggers and formation of vesicles that travel through BECs and exocytose cargo on the abluminal side of the BBB.

In one embodiment, the method of analyzing blood-brain barrier permeability characteristics of a test agent further comprises a step of measuring one or more effects of the test agent on the one or more target cells. For example, cell viability and/or cell function may be measured, for example, using a reporter system in the target cells.

In one embodiment, target cells are provided on opposite side of BBB to the side that is contacted with the test agent (e.g., bottom chamber). In this embodiment, effect(s) of the test agent (if it is able to pass the BBB) on the target cells may be assessed. For example, the effect of biologics and small molecules with neuroprotection effects can be evaluated on isogenic neurons with or without astrocytes following their transport through the BBB monolayer consisting of AF-iPSC-derived BECs. In one embodiment, target cells are reporter cells, which may be used to detect a cell phenotype or activation of a signaling pathway. In one embodiment, target cells may be isogenic with cells of the BBB.

In one embodiment, integrity of the seeded BEC monolayer is assessed visually prior to contacting the monolayer with the test agent.

Method of Visually Assessing Integrity of BEC Monolayer and/or BEC Monolayer Seeded on Support.

In one aspect, a method of visually assessing BEC monolayer integrity is provided. Visual assessment of the BEC monolayer is achieved by staining and/or labeling the BEC cells to visually distinguish live/dead cells and cell membranes. The stained/labeled cell monolayer is then visually assessed to determine whether there are substantial gaps (for example, gaps larger than the diameter of brain endothelial cells) between the cells. If one or more substantial gaps are present, the monolayer is not suitable for use in the BBB model.

In one embodiment, visual assessment of monolayer integrity is applied to a BEC monolayer seeded on a support. For example, BECs seeded on inserts in a Transwell system should be tightly packed, and cell monolayer uniformly established across the insert with no intracellular spaces larger than the diameter of brain endothelial cells present.

The method of visually assessing monolayer integrity provided herein may be referred to as "BBB View".

The present invention will be further illustrated in the following examples. However, it is to be understood that these examples are for illustrative purposes only and should not be used to limit the scope of the present invention in any manner.

EXAMPLES

Example 1: Reprogramming of Human AF Cells into iPSCs

Electroporation: $5.0 \times 10^5$ amniotic fluid (AF) cells were electroporated (nucleofected) with 1.3 pg of each plasmid (pEP4 E02S EN2K (Addgene—20925), pCEP4 M2L (Addgene—20926) and pEP4 E02S ET2K (Addgene—20927)), using the Nucleofector™ II Device Amaxa and the Basic Epithelial cell Nucleofector™ Kit (Lonza Cat #VPI 1005), using programs O-03 and $5.0 \times 10^5$ cells electroporated with program 1-03.

Electroporated cells were plated on a Matrigel-coated 6 well plate in DME+20% FBS and 10 μM Y27632 Stemolecule (Stemgent). Two days after electroporation, the medium was switched to mTeSR1 (Stem Cell Technologies). iPSC-like colonies started to appear on day 6 post-electroporation.

Preparation of human AF cells: Human AF cells were grown until 70-80% confluent. Spent medium was and cells were washed once with pre-warmed DMEM (Life Technology). Trypsin-EDTA (Life Technology) was added to cover the cell layer (2-3 mL) and the dish/flask was rocked gently. The dish/flask was left at room temperature until the cells started to detach (usually 2-5 minutes). Once the majority of cells were dislodged, growth medium was added and collected in a 15 mL conical tube. The dish/flask was rinsed with additional growth medium and collected in the same tube. The tube was centrifuged at 200 g for 5 minutes to pellet the cells and re-suspended in 2-4 mL of growth medium. 5.0×10⁵ cells were placed in 1.5 mL microcentrifuge tubes.

Nucleofection: DMEM supplemented with 20% FBS was pre-warmed to 37° C. The working Nucleofection solution was prepared by gently mixing 0.5 mL of the provided Supplement (XXX WHAT SUPPLEMENT XXX) to 2.25 mL Nucleofector Solution provided in the Nucleofector™ II Device Amaxa and the Basic Epithelial cell Nucleofector™ Kit (Lonza). Supplemented Nucleofector Solution was pre-warmed to room temperature and DNA for each sample was prepared. 2 mL of growth medium supplemented with 10 µM Y27632 Stemolecule was added to the appropriate number of wells of a 6-well plate previously coated with Matrigel; plates were pre-incubated in a humidified 37° C. and 5% $CO_2$ incubator. All incubations were carried out in a humidified 37° C. and 5% $CO_2$ incubator unless noted.

Figure 2:
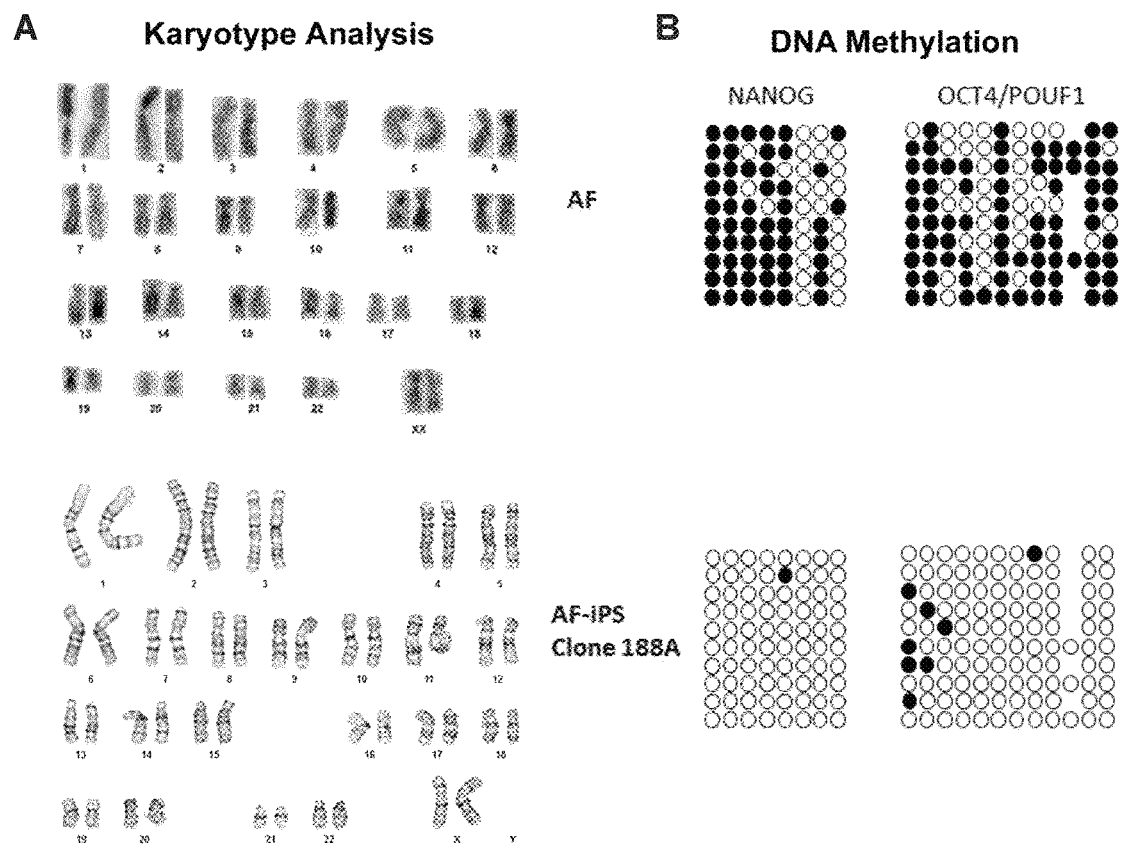
FIGS. 2A-B illustrate characterization of hAF-iPSCs.

AF26 cells were centrifuged at 200 g for 3 min in a microfuge centrifuge to form a pellet. Supernatant was completely discarded so that no residual medium covered the pellet. The pellet was immediately re-suspended in 100 µl room temperature Nucleofector Solution. 100 µl of cell suspension was mixed with the plasmid DNA. The sample was transferred into an Amaxa-certified cuvette. Cells were electroporated using programs O-03 or I-03 and then 500 µL of pre-warmed growth medium was added to the cuvette. Cells were transferred from the cuvette to the prepared 6-well plate incubated.

iPS colony isolation: The next day, survival rate of the nucleofected cells was determined and the medium was replaced with pre-warmed growth medium lacking the Y27632 Stemolecule. The following day, the medium was removed and 2 mL of pre-warmed mTeSR1 was added to each well. mTeSR1 was replaced daily and the cells were monitored for changes in morphology and colony formation. Once colonies reached a diameter between 200 and 500 µM, uniform, tightly-packed colonies were manually passaged. Individual colonies were transferred to a single well of a 12-well plate coated with Matrigel in mTeSR1 supplemented with 10 µM Y27632 Stemolecule and incubated. mTeSR1 was replaced every day, without addition of Y27632 Stemolecule. Individual clones were expanded by manually passaging all the colonies from a well when they reached 80% confluency, as described above. Areas comprising differentiating cells were removed before passaging the colonies. Colonies were transferred to six-well plates coated with Matrigel in mTeSR1 supplemented with 10 µM Y27632 Stemolecule and incubated.

iPSC clones were collected and characterized (FIG. 1). iPS clones were collected, live-stained with StainAlive Dylight 488 Mouse Anti human TRA-1-81 Antibody (Stemgent), and analyzed to assess pluripotency by Alkaline Phosphatase assay (FIG. 1A). Expression of pluripotent stem cell markers in AF-iPSCs vs. control amniotic fluid cells obtained at 26 weeks gestation (AF26) was assessed by Western blot analysis (FIG. 1B). The expression of OCT4, SOX2 and NANOG was several fold higher in AF-iPSCs compared with control AF cells (AF-26). Expression of OCT4, NANOG, SOX2 and KLF4 in AF-iPSCs was assessed by immunostaining (FIG. 1C) as was expression of stem cell markers by double-staining with TRA-1-81 and OCT4 (FIG. 1D). F-Actin and CD30 were also used in combination with OCT4 nuclear localization in AF-iPSCs (FIG. 1D). Teratoma assays or in vitro differentiation to all three germ layers (endoderm, ectoderm and mesoderm) followed by marker analysis by PCR and immunostaining, and karyotype-G-banding analysis (FIG. 2A) were also performed. Methylation assays were performed for some of the pluripotent markers (i.e. OCT4 and NANOG) to confirm the de-methylated state of the DNA (FIG. 2B).

hiPSC colonies were maintained by manually passaging colonies at a 1:6 (vol/vol) ratio in 6-well plates or 1:3 (vol/vol) ratio in 60-mm Matrigel-coated dishes in mTeSR1 supplemented with 10 µM Y27632 Stemolecule every 4-7 days until they were passaged two or three times. Thereafter, cells were passaged either manually or with Gentle Cell Dissociation Reagent (Stem Cell Technology) or frozen for long-term storage, as required. Areas of differentiation were removed before passaging. For long-term storage, all colonies were picked, centrifuged for 5 min at 200 g at room temperature, the pellet re-suspended in 3 mL of cryoprotective medium (mFreSR, Stem Cell Technology) and aliquoted in 1 mL portions/cryovial, then stored at −80° C. in a Nalgene cell freezing container, then transferred to a liquid nitrogen storage tank for long term storage.

Passaging iPSCs: When the colonies reached ~80% confluency, the medium was removed and gentle cell dissociation reagent (1 mL/well of a 6-well plate) was added. Cells were left at RT for 3-5 min while monitoring the dissociation of the colonies under a microscope. When the colonies started showing loosened packing, the gentle cell dissociation reagent was removed without disturbing the colonies. mTeSR1 was added to the wells (2 mL/well). Cells were gently scraped with a cell scraper and the aggregates collected in a 50 mL tube. The well was rinsed with 2 mL of pre-warmed mTeSR1 and collected in the same tube. Alternatively, 1 mL/well of ReLeSR (StemCell Technologies 05872) can be added for 30 seconds, and removed gently without disturbing the cells. mTeSR1 can be added to the wells (2 mL/well) and cells can be gently collected in a 50 mL tube. The well can be rinsed with 2 mL of pre-warmed mTeSR1 and collected in the same tube. This eliminates the need for manual removal (selection) of differentiated cells, and manual scraping of cells. Cells were plated at a 1:6 (vol/vol) ratio onto Matrigel-coated 6-well plates (or 1:3 in 60 mm dishes) and incubated. mTeSR1 was replaced daily. hAF-iPSCs can be maintained indefinitely as colonies in this manner or they can be differentiated as described below. After 10 or more passages, cells were transitioned to maintenance medium TeSR-E8. Colonies were passaged either manually or with enzyme-free dissociation reagents (ie. gentle cell dissociation reagent).

Example 2: Differentiation of Human AF-iPSCs into BECs

Protocol A: hAF-iPSCs were grown on Matrigel-coated 6-well plates in mTeSR1 for 3-5 days until 50-60% confluent. Medium was changed daily. Activated CSC Serum containing Medium (Cell Systems) was pre-warmed to 37° C. in a water bath. mTeSR1 (Stem Cell Technology) was removed and cells were washed once with pre-warmed DME/F12. Medium was removed and replaced with 2 mL/well pre-warmed activated CSC Medium. Cells were monitored daily and medium replaced every other day. Cells grew and started assuming a cobblestone-like morphology. The cells were passaged when they became very tight using either Gentle Cell Dissociation Buffer or Accutase (Stem Cell Technology), and were seeded at a 1:3 ratio in CSC medium supplemented with 10 µM Stemolecule Y27362. Endothelial cells were collected at different time points for RT-PCR, immunostaining, Western blot and other analyses.

Protocol B—adapted from Lippman et al (2012). hAF-iPSCs were grown on Matrigel-coated 6-well plates in 2 mL/well of mTeSR1 as described above for 3-5 days until 50-60% confluent. Medium was changed daily. mTeSR1 was removed and cells were washed once with pre-warmed KnockOut DME/F12. Medium was removed and replaced with 2 mL/well pre-warmed EB medium (for 100 mL): 78 mL KnockOut DMEM/F12 (Life Technologies), 20 mL KnockOut serum replacement (Life Technologies), 1 mL Glutamax (100×) (Life Technologies), 1 mL Non-essential Aminoacids (100×) (Life Technologies), beta-mercaptoethanol (Sigma) to a final concentration of 0.1 mM). After a few days, cells grew and started assuming a cobblestone-like morphology. Cells were maintained in EB medium for 5-7 days. Medium was removed and cells were washed once with Human Endothelial-SFM medium. Medium was removed and 2 mL/well of complete EM medium (Human Endothelial-SFM, Life Technologies), 1% Platelet-poor derived serum (PDS) (Biomedical Technologies Inc), 20 ng/mL bFGF (Life Technologies) was added. bFGF was added to the pre-warmed medium just before adding to the cells. Cultures were maintained in EM medium for a minimum of 5 days. Medium was replaced every other day. Confluent cells were passaged in complete EM medium on Matrigel coated plates or collagen/fibronectin matrix for further expansion and purification. EC cells were collected at different time points for RT-PCR, immunostaining, western blot and other analyses.

Example 3: Characterization of hAF-iPSC-BECs

Genetic Expression Profile of AF-iPSC-Derived BECs (Microarray)

In an effort to assess the genetic expression profile of AF-iPSC-derived BECs, microarray analysis was performed on a population of AF-iPSC-derived BECs.

The 435 genes provided on the custom microarray include: ABCA1 (ABC1); A2M; ABCA10; ABCA12 (1); ABCA12 (2); ABCA13; ABCA2; ABCA3; ABCA4; ABCA5; ABCA6; ABCA7; ABCA8; ABCA9; ABCB1 (MDR-1 PGP); ABCB10; ABCB11; ABCB4; ABCB5; ABCB6; ABCB8; ABCB9 (1); ABCB9 (2); ABCC1; ABCC10; ABCC11; ABCC12; ABCC13 (1); ABCC13 (2); ABCC2; ABCC3; ABCC5; ABCC8; ABCC9; ABCD2; ABCD3; ABCD4 (ALD); ABCF1; ABCF2; ABCF3; ABCF3(GCN20); ABCG1; ABCG2; ABCG4; ABCG5; ABCG8; ACCN4; ACTB; AGER; AKAP12 (gravin); ALPI; ALPL; ALPP; ANGPT1 (V1); ANGPT1 (V1); ANGPT1 (V2); ANO4 (TMEM16D); ANO6 (TMEM16F); ANO9 (TMEM16J); AP2A2; APOB; APOE; APOL1; AQP10; AQP2; ARL6IP5; ATF1; ATP11C; ATP13A4; ATP1A1; ATP1A2; ATP1A3; ATP1B1; ATP1B3; ATP2A2; ATP2B1; ATP2B3; ATP6V0D1; ATP6V1B1; ATP7A; ATP8B1; ATP8B2; ATP8B4; BCAP31; BEST4 (VMD2L2); BPIFA2; BSG; CACNA1A; CACNA1C; CACNA2D1; CACNB2; CAV1; CCL2; CD36; CDH12; CDH5; CFL1; CFTR; CFTR/MRP (ABCC6); CGN; CHRNA5; CKB; CLCA1; CLCN1; CLCN3; CLDN1; CLDN3; CLDN5; CLIC1; CNGB1; CNTNAP2; CNTNAP4; CNTNAP5; COL4A1; COL4A2; COL4A4; COLEC12 (SRCL); CPE; CPNE3; CPNE7; CST3; CTNNB1; CTNND1; CTTN; CUBN; CYB5-M; DENND5A (RAB6IP1); DENND5B; EEA1; EFEMP1; ENG; ENT3 (SLC29A3); ENT4 (SLC29A4); EPAS1; ESAM; F11R; F5; FGF19; FGG; FLT1; FN1; GABRA2; GAPDH; GFAP; GGA1; GGTL4; GPRC6A G; GRIK3; GRIN1; GRIN2A; GUSB; HBA1; HHIPL2; HIF1A; HIST2H2AA4; HMBS; HPRT1; ICAM-1(CD54); IGF1R; IGF2 (somatomedin A); IGF2R; IGFBP1; IGFBP2; IGFBP3; IGFBP4; IGFBP5; IGFBP6; IKBKE; IL1B; IL8; INSR; ITPR2; ITPR3; JAM2; JAM3; JUP (CTNNG); KCNA5; KCNA7; KCNH1; KCNH5; KCNK10; KCNMB2; KCNQ2; KCTD16; KDR; LAMA1; LAMA3; LAMA4; LAMB1; LAMB2; LAT1-3TM; LCN1; LRP1; LRP10; LRP11; LRP2; LRP3; LRP4; LRP5; LRP6; LRP-8; LU; M6PR; MACF1; MAGT1; MAOB; MAP1A; MAP1B; MARCO; MB; MBP; MCOLN1; MCP; MCT1 (SLC16A1); MCT2 (SLC16A7); MCT3 (SLC16A8); MF12; MFSD2A; MLLT4 (AF6); MMP12; MMP13; MMP14; MMP2; MMP3; MMP7; MMP8; MMP9; MPZL1; MPZL2 (EVA1); MRP4, ABCC4; MSR1; MVP; MYO5A; NFKB1; NFKBIA; NRP1; NRP2; NRXN1; NRXN2; OATP-H (SLC21A12; SLCO4C1); OATPRP3 (SLCO3A1); OCLN; OSTalpha; OSTbeta; P2RX4; PARD3; PECAM-1 (CD31); PES1; PGK1; PKD1; PLAT; PLP2; PLSCR1; PLSCR3; PLSCR4; PODXL; POP4; PPIA; PPIB; PRAF2; PRG1; PROCR; PROM1; PROM2; RAB3D; RAB5A; RAMP2; REEP2; REEP5; REEP6; RPH3A; RPL30; RPL37A; RPLP2; RYR2; S100A6; S100B; SCARA3; SCARB1; SCARB2; SCN10A; SCN3A; SCN4B; SCN7A; SCN8A; SEC61A1; SEC61A2; SELE; SHROOM3; SLC10A6 (SOAT); SLC11A2; SLC12A2; SLC12A7; SLC15A1; SLC15A1; SLC15A2; SLC16A1; SLC16A10; SLC16A11; SLC16A2; SLC16A3; SLC16A4; SLC16A5; SLC16A6; SLC17A1; SLC17A2; SLC17A3; SLC17A4; SLC17A5; SLC17A6; SLC17A7; SLC17A8; SLC18A1; SLC18A2; SLC1A1; SLC1A2; SLC1A3; SLC1A4; SLC1A5 (ASCT2); SLC1A6; SLC1A7; SLC21A14; SLC21A8; SLC22A1 (hOCT1); SLC22A10; SLC22A11; SLC22A12; SLC22A13; SLC22A14; SLC22A15; SLC22A17; SLC22A18; SLC22A1LS; SLC22A2; SLC22A3; SLC22A4; SLC22A5; SLC22A7; SLC22A8 (hOAT3); SLC22A9; SLC26A5 (Prestin); SLC26A8; SLC28A1 (CNT1); SLC28A1(CNT1); SLC28A3; SLC29A1; SLC29A1; SLC29A2; SLC2A1; SLC2A10; SLC2A11; SLC2A12; SLC2A13; SLC2A14; SLC2A4; SLC2A5; SLC2A6; SLC2A8; SLC2A9; SLC30A1; SLC30A8; SLC35B2; SLC35B4; SLC37A4; SLC38A1; SLC38A2 (ATA2); SLC38A4; SLC3A2; SLC41A2; SLC44A3; SLC5A10; SLC5A7; SLC6A13; SLC6A6; SLC7A1; SLC7A2; SLC7A3; SLC7A4; SLC7A5; SLC7A6; SLC7A7; SLC7A8; SLC7A9; SLC9A5; SLC9B1; SLCO1A2; SLCO1B1; SLCO2A1; SLCO2B1; SLCO3A1; SLCO4A1; SLCO5A1; SLCO6A1 (OATP-I mRNA); SMARCA4; SORCS1; SORCS3; SORL1; SPARC (osteonectin); STAB1; SUSD1; SVOPL; SXR (NR1I2); SYPL1; TAP1; TAP2; TAPBP; TFR2; TFRC; THBS2; TIMP1; TIMP2; TIMP3; TIMP4; TJP1; TJP2; TJP3; TMEM30A (CDC50); TNF-a; TOM1L1; TRPC3; TRPC4; TRPM2; TRPM3; TRPM7; TRPV5; TUBA3; VCAM1; VEGF-A; VIM; VLDLR; VWF; WNK1; YBX3 (CSDA); ZER1; and SOX17.

Microarrays were printed by NRC, accordingly to published methods (Pen et al., 2007, Molecular markers of extracellular matrix remodeling in glioblastoma vessels: microarray study of laser-captured glioblastoma vessels, Glia. 2007 Apr. 15; 55(6):559-72). cDNA synthesis, DNA hybridization and wash were carried out according to 3DNA array detection 900 kit recommendations. Scanning of the microarray slide(s) were carried out on a Genepix scanner according to manufacturer's protocols. See the above-mentioned reference.

Figure 3:
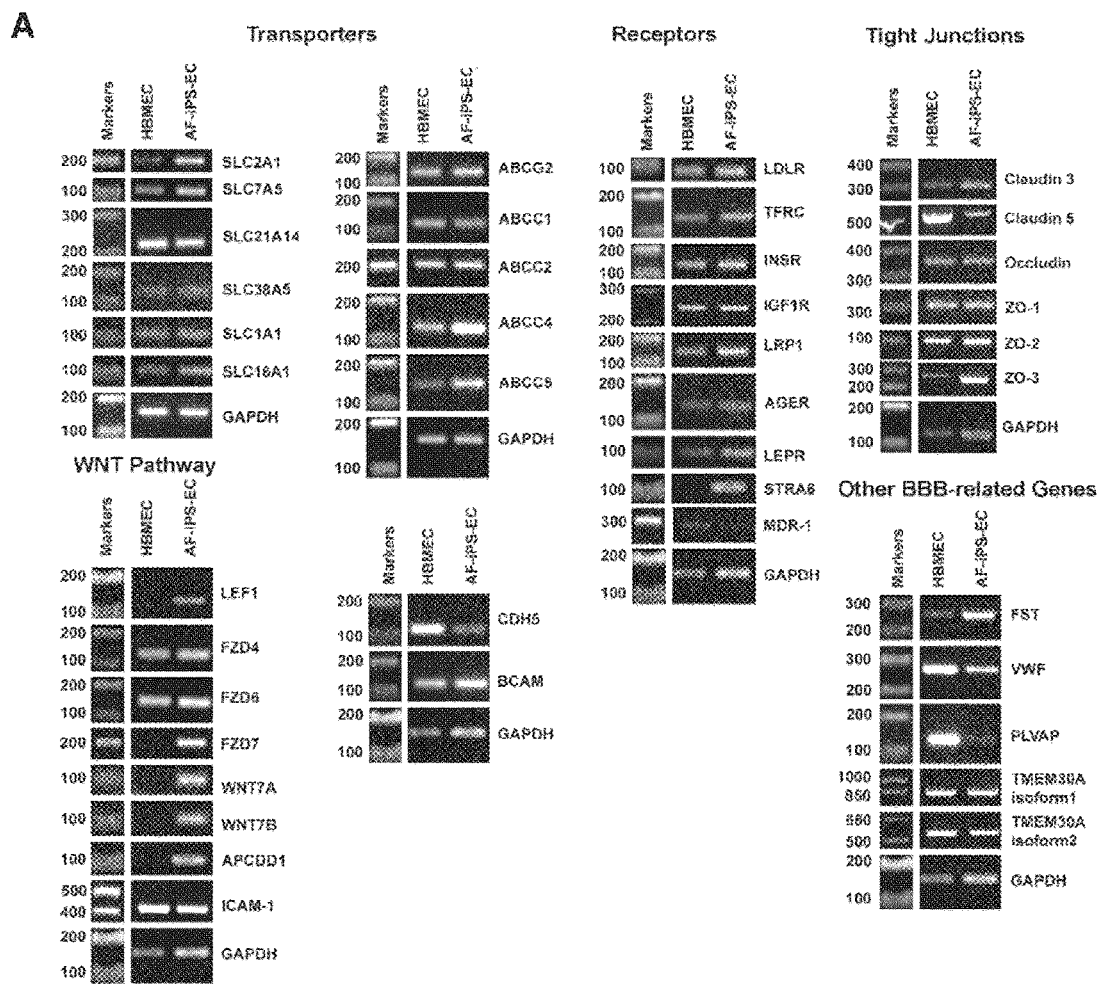
FIGS. 3A-D depict characterization of hAF-iPSC-BECs.
Figure 3:
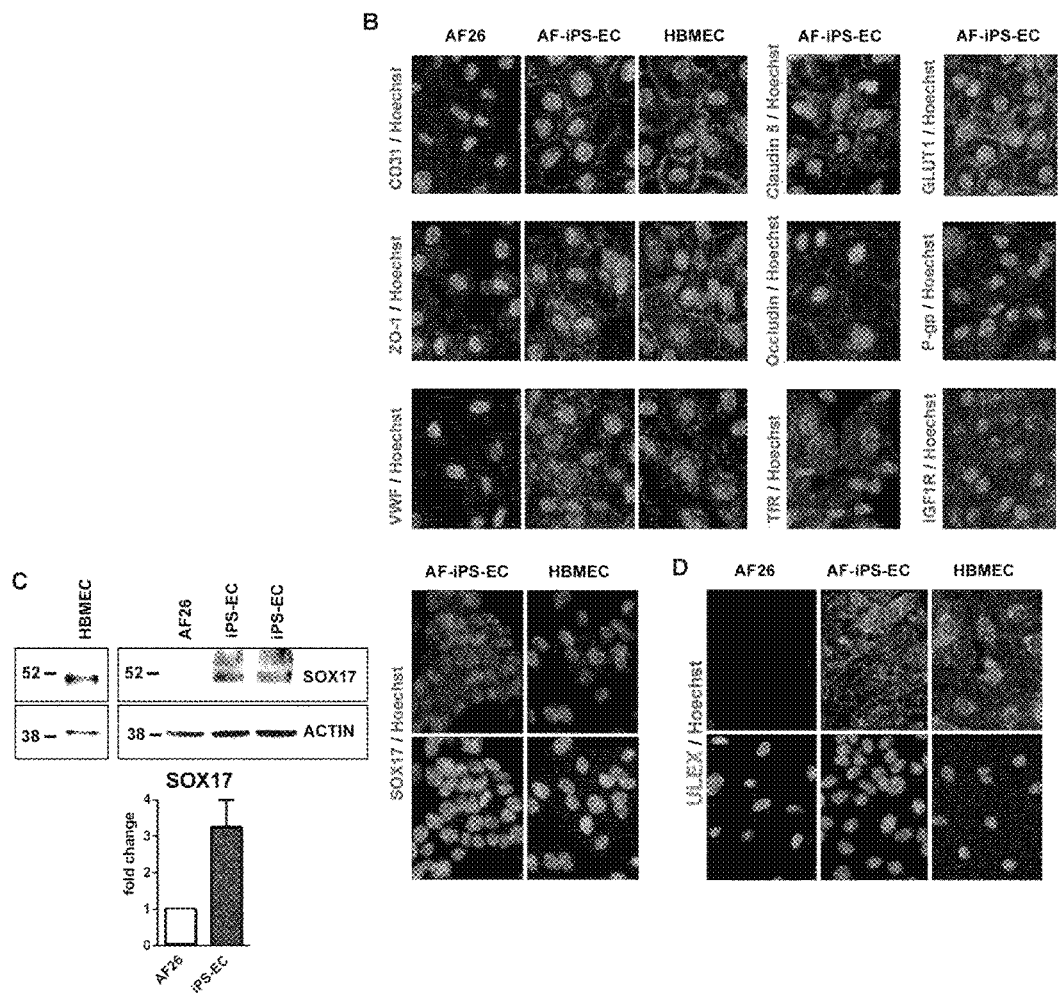

The expression profile of AF-iPSC-derived BECs was compared to that of HBMECs (Cell Systems) to determine similarities and differences in gene expression profiles by BBB microarray analysis, data not shown) and RT-PCR (FIG. 3A). About 93% of the genes in the BBB microarray (total number of genes=435) were expressed in AF-iPSC-derived BECs, confirming their relevance to BBB (data not shown). The expression of many of these genes was further evaluated by RT-PCR (FIG. 3A). Various SLC and ABC transporter and receptor genes were similarly expressed by both HBMECs and AF-iPSC-derived BECs, confirming the brain endothelial nature of AF-iPSC-BECs (FIG. 3A). Expression of the following genes distinguishes AF-iPSC-BECs from the other BECs tested: FZD7, WNT7A, WNT7B, APCDD1, STRA6 and ZO-3.

AF-iPSC-BECs were further characterized relative to control AF cells (AF26) and HBMECs by staining for BEC markers (FIGS. 3B-D) and Western blotting (FIG. 3C).

Gamma GTPase in AF-iPSC-BECs.

Figure 4:
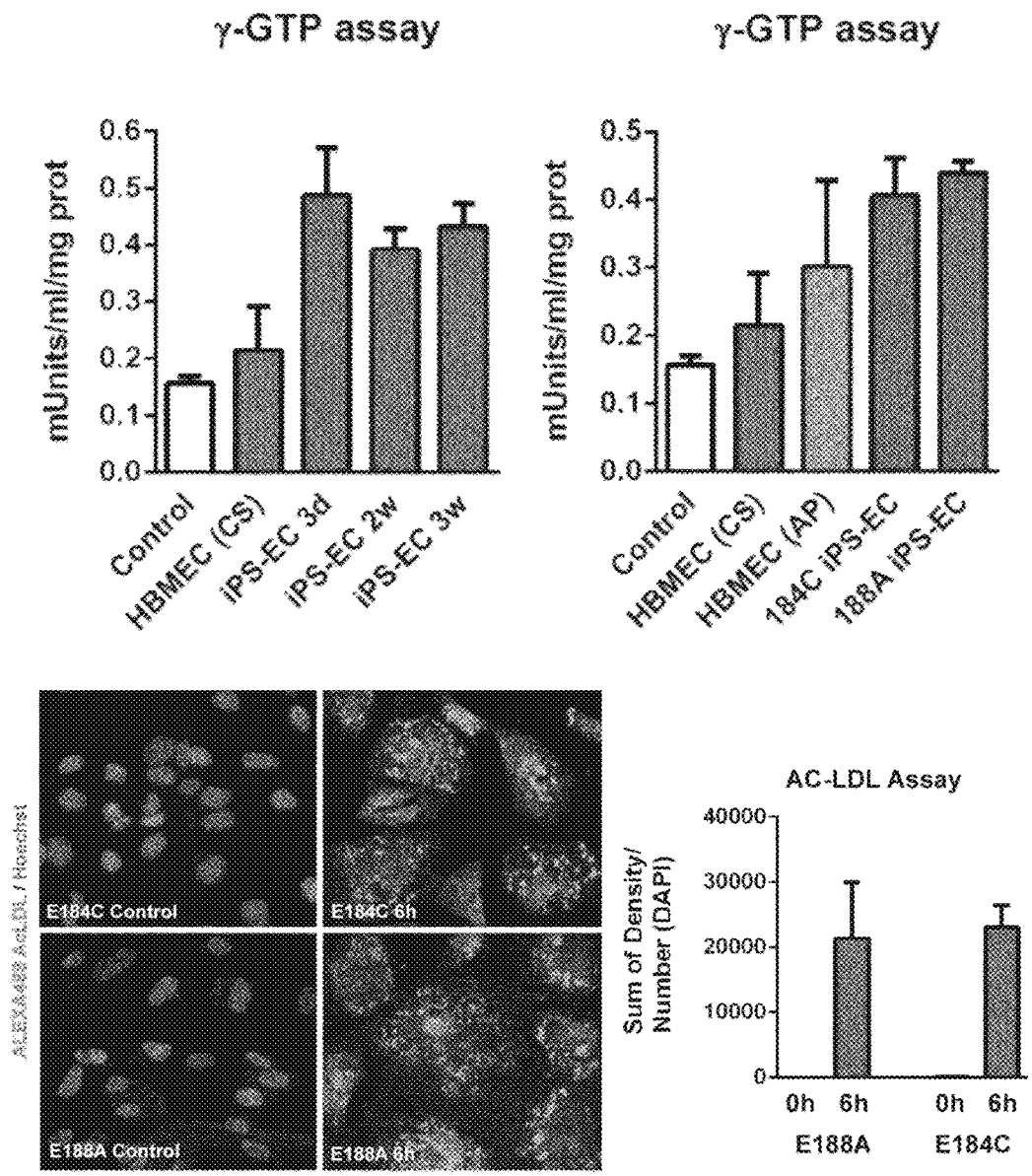
FIG. 4 illustrates Gamma GTPase in AF-iPSC-BECs. Top left of FIG. 4 depicts Gamma GTPase in AF-iPSC-BECs after 3 days, 2 weeks and 3 weeks (iPS-EC 3d, 2w, 3w, left panel). Top right panel shows two different clones of AF-iPSC-derived brain endothelial cells (184C iPSC-EC and 188A iPSC-EC) compared with HBMECs from Cell Systems (CS) and AngioProteomie (AP). Bottom panel depicts acetylated LDL in AF-iPSC-derived brain endothelial cells (clones 184C and 188A) at times 0 and 6 hours.

Gamma GTPase in AF-iPSC-BECs was examined after 3 days, 2 weeks and 3 weeks (iPS-EC 3d, 2w, 3w; FIG. 4, left panel). Two different clones of AF-iPSC-BECs (184C iPSC-EC and 188A iPSC-EC) were compared with HBMECs from Cell Systems (CS) and AngioProteomie (AP) (FIG. 4, top right panel). The positive control used was provided in the gamma GTP assay kit (Sigma). Acetylated LDL was analyzed in AF-iPSC-BECs (clones 184C and 188A) at time 0 and 6 hours (FIG. 4, bottom panels).

Capillary-Like Tube Formation by AF-iPSC-BECs.

Figure 5:
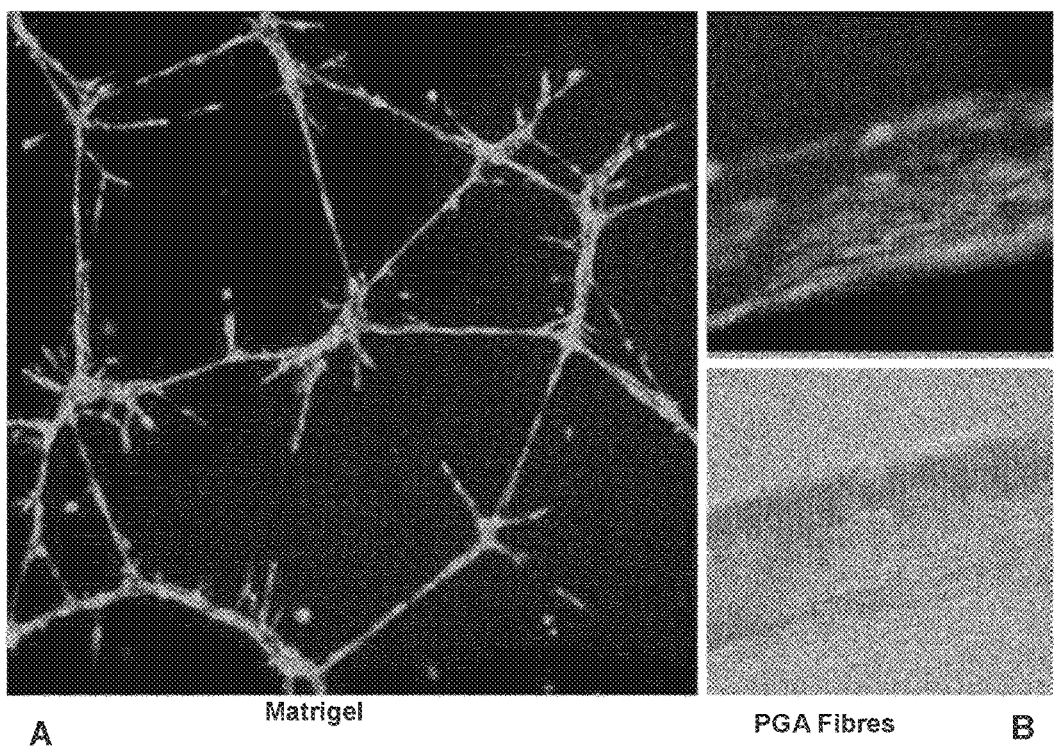
FIGS. 5A-B depict in vitro formation of capillary-like structures by AF-iPSC-BECs.

Formation of capillary-like structures by AF-iPSC-BECs in vitro was assessed on Matrigel (FIG. 5A) and on PGA (FIG. 5B), a polymer used clinically for transplantation and approved by Health Canada and FDA. AF-iPSC-BECs were stained with CFDA (a cell survival marker). AF-iPSC-BECs formed capillary-like structures on both substrates tested.

Example 4: Generation of a Human Blood Brain Barrier Model Comprising AF-iPSC-BECs After 5 days of culture in complete EM medium, the AF-iPSC-BECs were ready for use in a Transwell system.

For example, a Transwell system comprising of permeable support for 12 well plate inserts with 1.0 µm transparent PET membrane (Falcon 353103) and 12 well cell culture companion plates (Falcon 353503). The number of inserts needed are estimated based on the number of wells of AF-iPSC-BECs to be passaged. For example, a T-75 of AF-iPSC-BECs can give rise to about 9 million cells. Thus, 18 inserts (500 thousand cells/insert) would be needed.

Sterile inserts were transferred to the 12 well cell culture companion plates using sterile forceps. All inserts were visually inspected prior to use. PET membrane was stretched and pulled tight. Membrane was be cut to size along outer edge of plastic molding. Inserts that did not meet these criteria were discarded (e.g., if surface was wrinkled or puckered, mesh was cut short of outer edge of plastic molding or extended beyond it). Discard rate was at 10-15%, but may vary per lot number. At least 3 extra inserts were prepared to be used as background when measuring transendothelial electrical resistance (TEER). Each insert was coated with 500 µL of pre-warmed 0.5% gelatin (Sigma G1890) and inserts were incubated at 37° C. overnight.

The following day, the complete EM medium was removed from AF-iPSC-BECs, accutase was added (1 mL/well of 6 well plate) and incubated at 37° C. for 5 minutes. The cells were monitored under the microscope to assess dissociation. The detached cells were transferred to a sterile 50 mL conical tube by pipetting them through a sterile 40 µm strainer (Falcon 352340). Pre-warmed DMEM/F12 with Glutamax (2 mL/well of 6 well plate) was added to wash the wells and harvest any remaining cells then transferred to the same 50 mL conical tube by pipetting through the sterile 40 µm strainer. The cells were counted using a hemacytometer and were centrifuged at 300 g for 5 minutes. The supernatant was removed and an appropriate volume of complete EM medium supplemented with 10 µM of Y-27632 was added to the cells based on the cell count. The 0.5% gelatin was aspirated from inserts and cells were plated at 500 thousand cell/insert in 1 mL of complete EM medium. 2 mL of complete EM medium was added to the bottom chamber under each insert in the 12 well companion plate and incubated. The medium was replenished every 24-48 hours.

Measuring Integrity of AF-iPSC-BECs in BBB Transwell System

Figure 6:
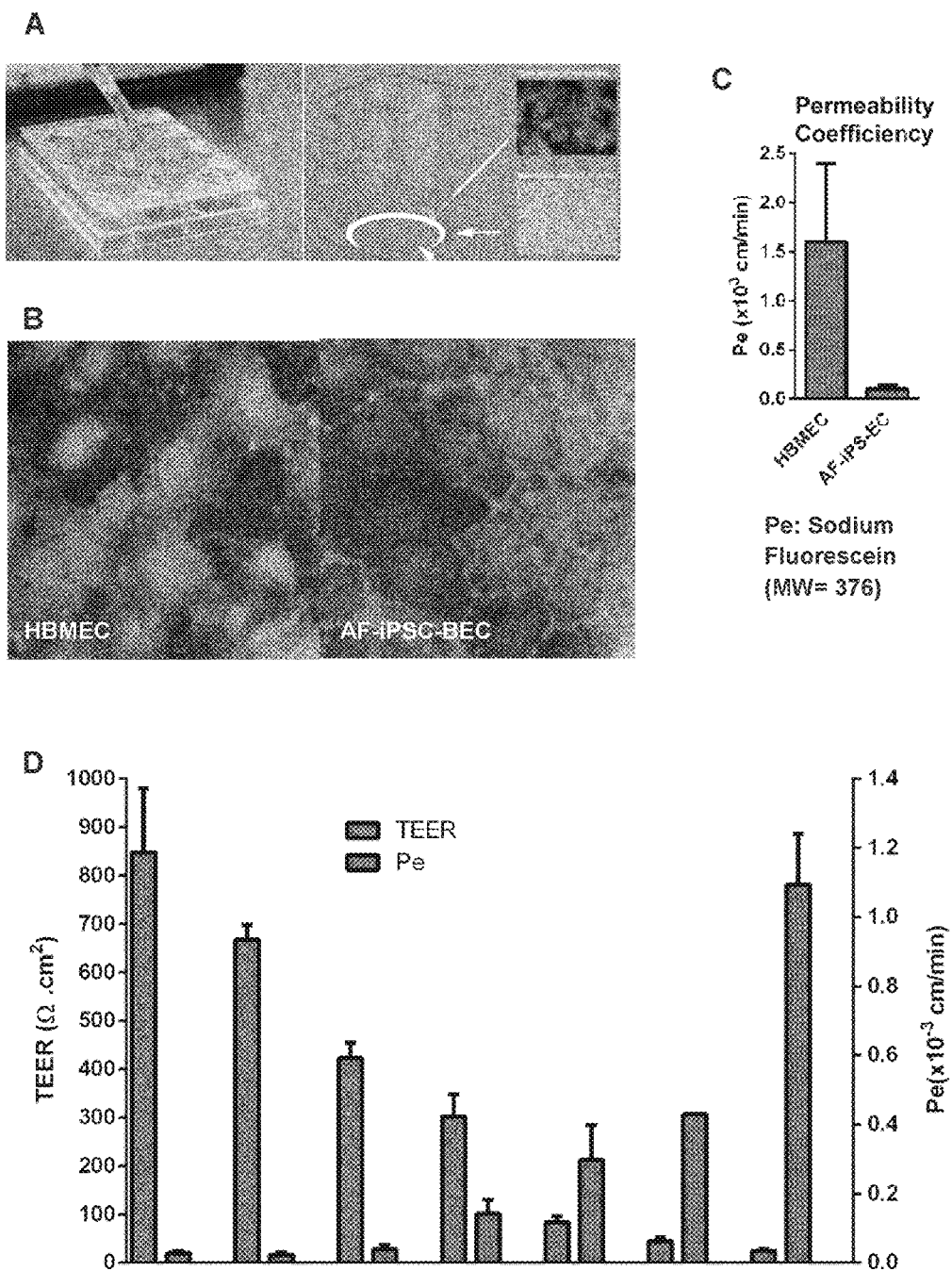
FIG. 6A-E illustrate assessment of blood brain barrier integrity in a monolayer comprising AF-iPSC-BECs.
Figure 6:
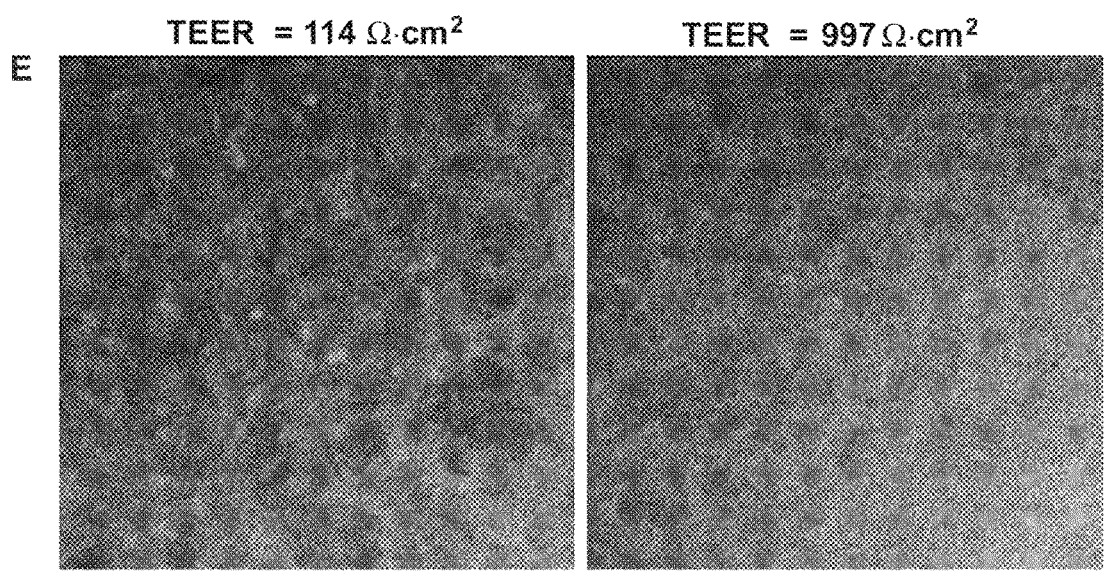

Cells were examined under the microscope to assess cell morphology and cell monolayer integrity. Cells should be tightly packed and cell monolayer uniformly established across the insert, no intracellular spaces larger than the diameter of brain endothelial cells present. For example, in an in vitro BBB transwell system (FIG. 6A) AF-iPSCs on an insert were live-stained with CFDA and CMO fluorescent dyes and an image of the stained BBB was obtained (FIG. 6B). CFDA shows cell survival and CMO shows cell-cell contact. This method of staining and imaging was used to assess the integrity of the BBB, wherein if intracellular spaces larger than the diameter of BECs were present, the BBB was deemed insufficient for use. This method, generated by the inventors, is referred to as BBB View.

We also examined AF-iPSC-BECs and HBMECs (Cell Systems to determine sodium fluorescein permeability of the BBBs (FIG. 6C). Sodium fluorescein permeability of AF-iPSC-BECs was significantly lower than that of HBMECs.

TEER measurements were taken to assess the integrity of tight junction dynamics of the AF-iPSC-BECs monolayer. TEER measurements were done on each insert to assess cell monolayer "tightness". TEER values must be 400 $\Omega \cdot cm^2$ to meet "tightness" criteria and to proceed to experimental transport assay the same day. The CellZScope (Nanoanalytics serial #CZS0110814) with CellZScope Software version 2.2.2 on a Lattitude E6400 Laptop, 24 well cell module with 1 cm diameter electrodes was used to measure TEER. Standard spectrum settings: Frequency 1 HZ-100 KHZ, points per decade 9, spacing logarithmic. The 24 well cell module was per-warmed for at least 6 hours at 37° C. before reading TEER. The inserts with hAF-iPSC-BECs were transferred into the module well, and 1.5 mL of complete EM medium was added to the bottom chamber of the module. The chamber was placed back in incubator and attached to the external controller. CellZScope software was used to measure TEER using a single run. Cell inserts with TEER value 400 $\Omega \cdot cm^2$ can be used for transwell assays.

The correlation between TEER values and sucrose Pe for AF-iPSC-BECs (N=11) is provided in FIG. 6D. The highest TEER value obtained in this model was 1200 Ohm. cm 2. The correlation between TEER value and BBB integrity, as assessed by BBB view is provided in FIG. 6E, wherein the left panel represents a low TEER value that is associated with a poor BBB monolayer, as indicated by the gaps among cells grown in the insert. In contrast, a well-integrated BBB monolayer has a higher TEER, as indicated by the lack of gaps in the monolayer in the right panel of FIG. 6E. The correlation between TEER value and BBB integrity shows that BBB View can be used as a rapid and efficient method to define the quality of a BBB.

Figure 7:
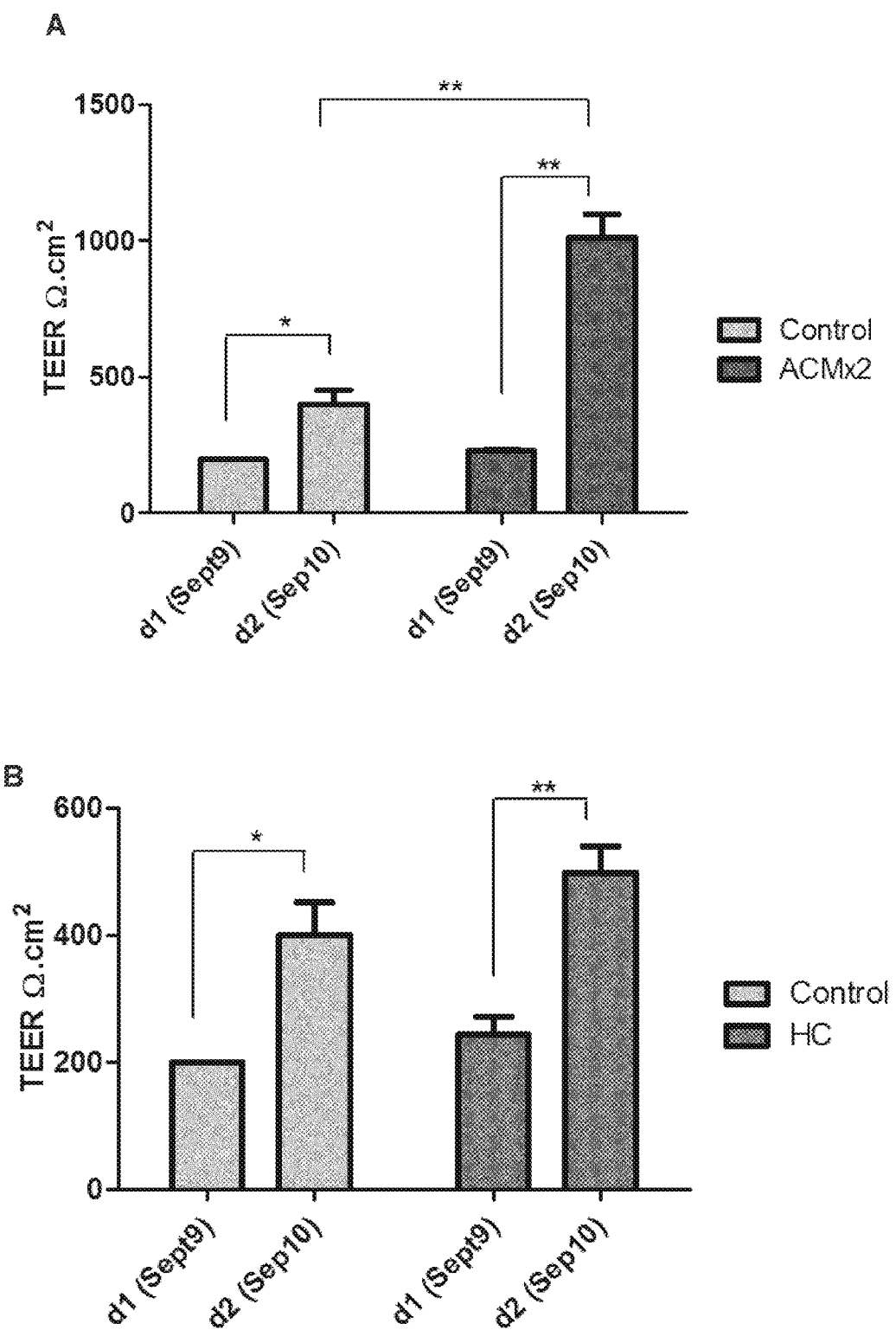
FIGS. 7A-B depict TEER values of AF-iPSC-BECs cultured under different conditions.

Use of Conditioned Medium and/or Chemicals to Increase TEER Values of AF-iPSC-BEC BBBs In an effort to increase the tightness of the BBB model provided herein, the model was cultured in astrocyte conditioned media (ACMx2) for 24 hours. Within 24 hours, the BBB model comprising AF-iPSC-BECs cultured in ACMx2 showed a significant increase in TEER value (FIG. 7A). Similarly, the model was cultured in the presence of hydrocortisone (HC), which resulted in a significant increase in TEER value (FIG. 7B).

Use of the AF-iPSC-BEC BBB Model to Analyze BBB Permeability of a Test Agent

The in vitro BBB model comprising AF-iPSC-BECs was tested for transporting small molecules, such as diazepam and cyclosporine, across the barrier (See Garberg et al., 2005, In vitro models for the blood-brain barrier for reference, Toxicol In Vitro. 2005 April; 19(3):299-334).

As an example of measuring transcytosis of a test compound on hAF-iPSC-BECs monolayer, experimental in vitro BBB transport assay—top to bottom is described as follows: 1× transport buffer (TB) (50 mL 10×TB 50 mM in 450 mL HBSS—5.95 g HEPES, 2.54 g $MgCl_2 \cdot H_2O$ and HBSS were prewarmed to 37° C. Bottom of inserts with hAF-iPSC-BECs were washed in HBSS by dipping inserts in pre-warmed 2 mL of HBSS three times. Inserts were placed in 2 mL/well of pre-warmed 1×TB. Medium was removed from each insert without disturbing the monolayer. 500 µL of pre-warmed 1×TB was added to each insert. Compound to be tested was prepared in 1×TB as a 2× input solution. 500 µL of 2× input was added to each insert (3 inserts per compound being tested) and inserts were incubated at 37° C. on gently rotating platform (20 rpm). 200 µL was collected from the bottom chamber into sample collection tubes at 30, 60, 90 and 120 minutes. 200 µL of 1×TB was added back to the bottom well of all inserts after each collection. A number of methods can be used for quantitative sample analysis such as MRM, ELISA, and functional activity assays. Results of the experiments are provided in the following table:

are a measure of the specific permeability of the compound across brain endothelial monolayer.

Absolute quantitation of $V_HH$ using MRM-ILIS method. The methods used were as described in Haqqani et al. (2012). Briefly, to develop the SRM (selected reaction monitoring also known as multiple reaction monitoring (MRM)) assay for VHHs, each $V_HH$ was first analyzed by nanoLC-MS/MS using data-dependent acquisition to identify all ionizible peptides. For each peptide, the 3 to 5 most intense fragment ions were chosen. An initial SRM assay was developed to monitor these fragments at attomole amounts of the digest (about 100-300 amol). Fragments that showed reproducible intensity ratios at low amounts (i.e., had Pearson r2≥0.95 compared to higher amounts) were considered stable and were chosen for the final SRM assay. To further optimize the assay, elution times for each peptide were also included, with care taken to not choose peptides that have close m/z (mass-to-charge ratio) and elution times.

Figure 8:
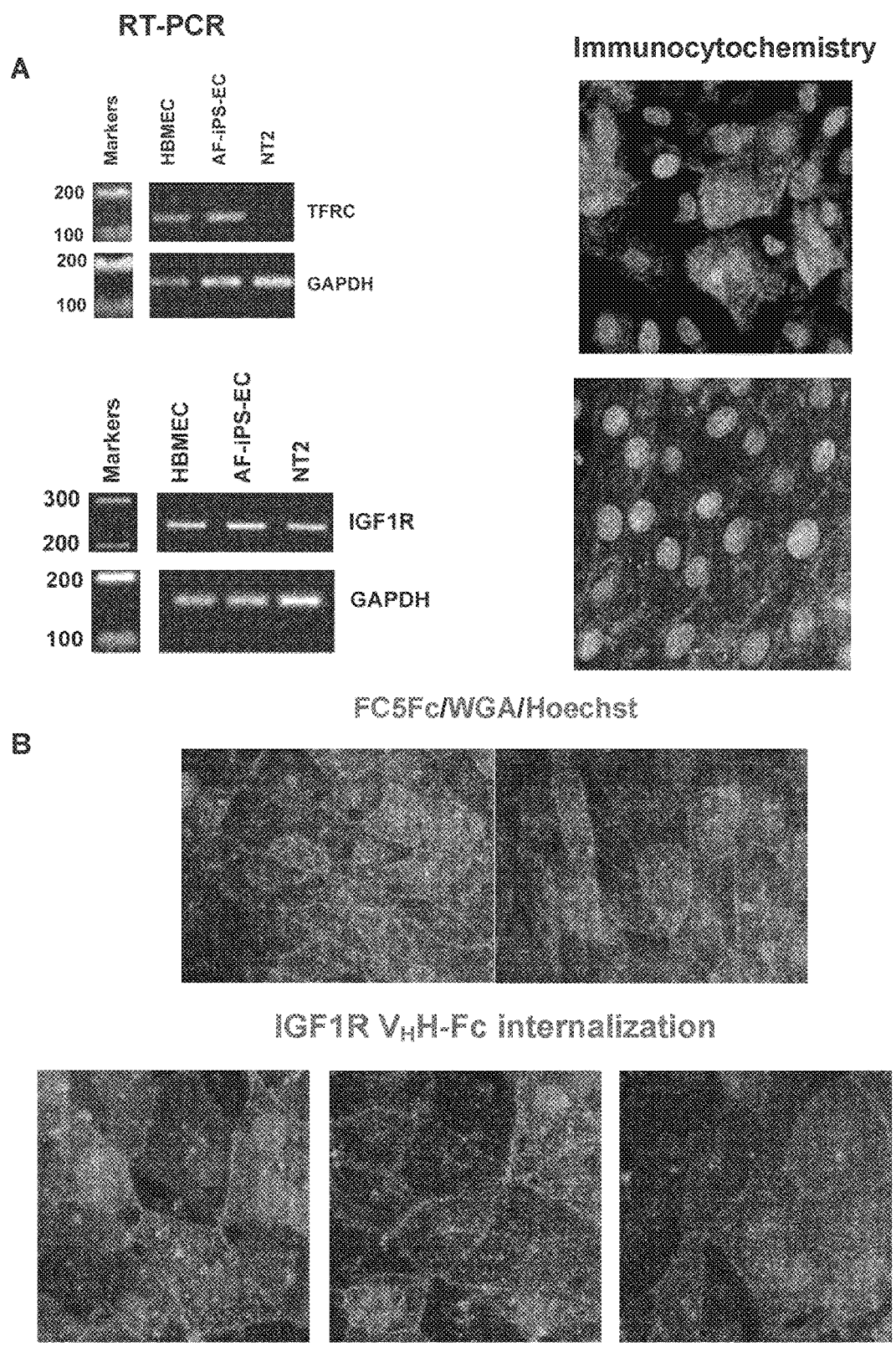
FIGS. 8A-E depict analysis of test agent movement across a BBB.
Figure 8:
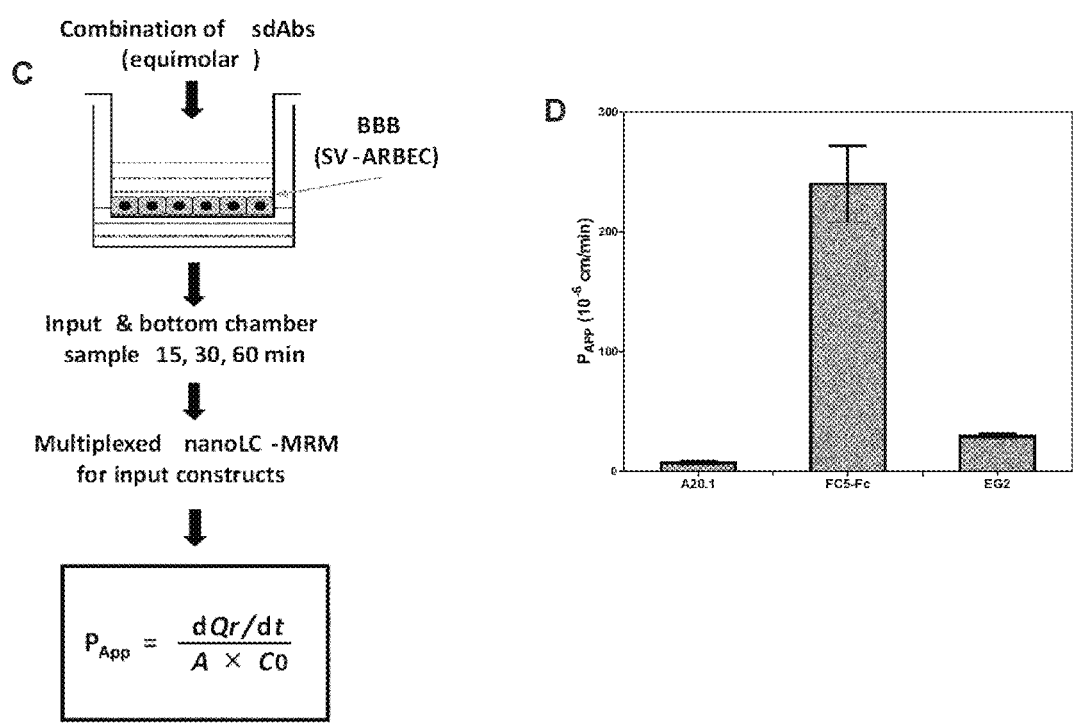
Figure 8:
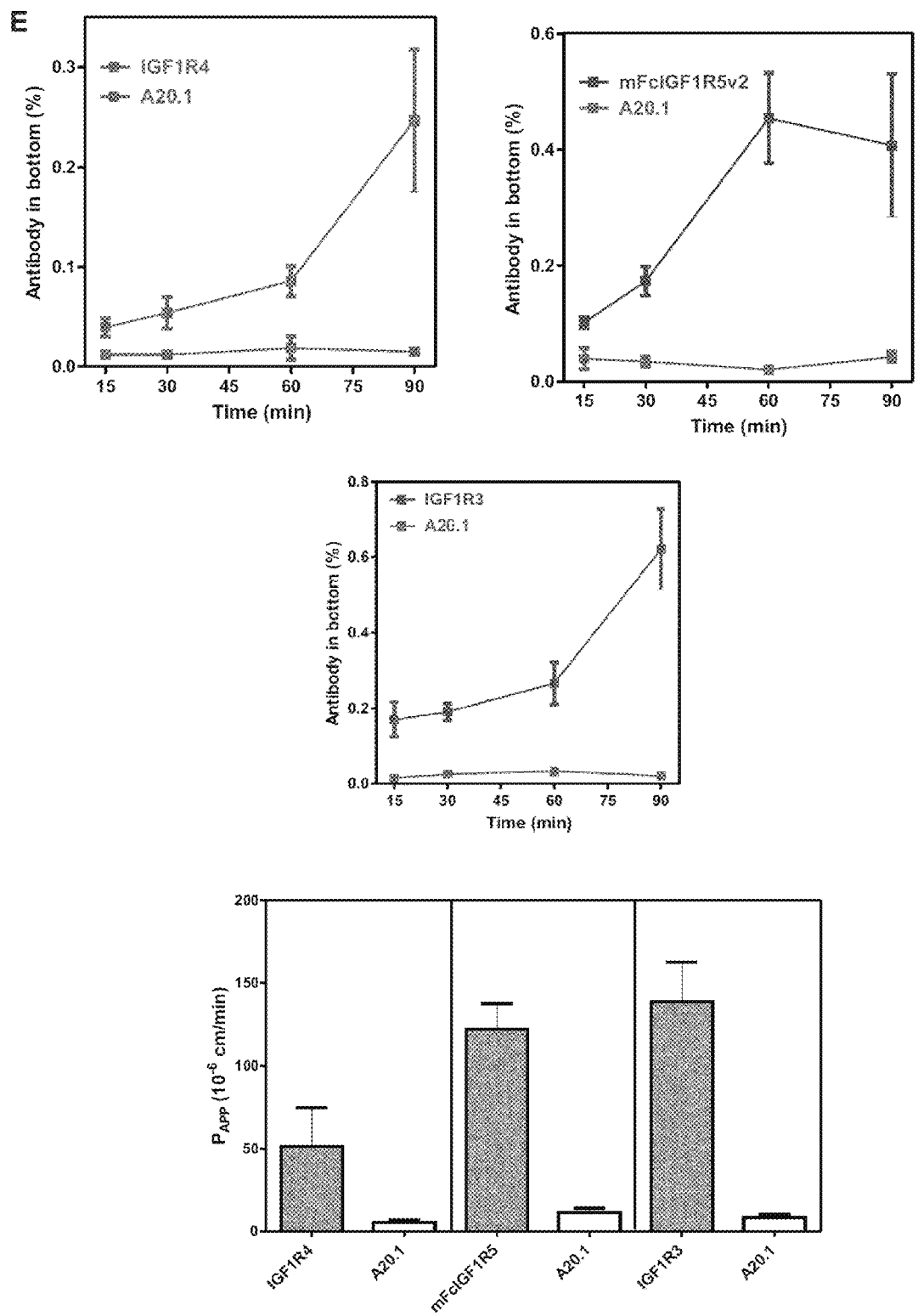

Expression of receptor-mediated transcytosis (RMT) receptors, transferrin receptor (TfR) and insulin growth factor-1 receptor (IGF1R) in AF-iPSC-BEC as measured by RT-PCR and immunochemistry was confirmed (FIG. 8A). Internalization of antibodies recognizing RMT receptors into AF-iPSC-BEC (receptor-mediated endocytosis) was confirmed (FIG. 8B). FC5, IGF1R3, IGF1R4, and IGF1R5 are lama single domain antibodies shown to cross BBB via a receptor-mediated transcytosis (PCT/CA2001/000783, PCT/CA2014/000860, PCT/CA2014/000861, PCT/CA2014/000862, respectively) and to cross-react among rodent and human RMT receptors. VHHs were fused with an Fc antibody fragment as described, labeled with the fluorescent dye Alexa 555.

Use of the in vitro BBB model provided herein to assess the ability of various $V_HHs$ to cross the BBB is summarized

| Permeability Coefficient(Pe) Summary: Rat and Human in vitro BBB models | | | | | | | | |
|---|---|---|---|---|---|---|---|---|
| | | | | Transport top to bottom A > B | | Transport top to bottom B > A | | Pe Ratio |
| Compound | MW | Model | Expt | Pe(×10⁻³) cm/mm) | StDev | Pe(×10⁻³) cm/mm) | StDev | B > A / A > B |
| ³H-Diazepam | 287 | Rat (SV-ARBEC) | 2001 ECVAM | 2.03 | | 0.41 | | 0.20 |
| | | Human (AF-iPS-EC) | 4 Feb. 2015 P9 | 1.47 | 0.22 | | | |
| ³H-Cyclosporine A | 1203 | Rat (SV-ARBEC) | 26 Nov. 2014 | 0.069 | 0.024 | 0.201 | 0.087 | 2.93 |
| | | | 2001 (ECVAM) | 0.086 | | 0.259 | | 3.01 |
| | | Human (AF-iPS-EC) | 10 Jul. 2015 P9 | 0.192 | | 0.501 | 0.051 | 2.61 |

| Apparent Permeability(Papp) Summary: Rat and Human in vitro BBB models | | | | | | | | |
|---|---|---|---|---|---|---|---|---|
| | | | | Transport top to bottom A > B | | Transport top to bottom B > A | | Papp Ratio |
| Compound | MW | Model | Expt | Papp(×10⁻³) cm/mm) | StDev | Papp(×10⁻³) cm/min) | StDev | B > A / A > B |
| | | Human (AF-iPSC-EC) | 4 Feb. 2015 P9 | 0.166 | 0.041 | | | ND |
| | | | 24 Mar. 2015 P9 | 0.028 | 0.004 | | | ND |
| ³H-Diazepam | 287 | Human (AF-iPSC-EC) | 5 Feb. 2015 P9 | 1.198 | 0.158 | 0.966 | 0.157 | 0.806 |

Transport of the IGF1R-5 Across In Vitro Blood Brain Barrier Model

Determination of the apparent permeability coefficient: Quantified values can be directly plotted or the $P_{app}$ (apparent permeability coefficient) values can be determined with the given formula (FIG. 8C) and plotted. The $P_{app}$ value is commonly used to determine the ability of a molecule to cross the BBB. [Qr/dt=cumulative amount in the receiver compartment versus time; A=area of the cell monolayer; C0=initial concentration of the dosing solution]. $P_{app}$ values in FIG. 8C. Briefly, equimolar amounts (1.25 µM) of positive (FC5, IGF1R-3, IGF1R4, IGF1R-5 or their fusion with Fc) and negative control (A20.1, a *Clostridium difficile* toxin A-binding $V_HH$; and EG2, an EGFR binding $V_HH$) $V_HHs$ were tested simultaneously for their ability to cross a monolayer of AF-iPSCs-BEC on the gelatin-coated membrane of an insert. Following co-addition of equimolar amounts of the various $V_HH$ to the luminal side of the BBB model, samples were taken from the bottom chamber after 30, 60, 90, and 120 min. The concentrations of each $V_HH$ were then quantified by mass spectrometry (multiple reaction monitoring—isotype labeled internal standards; MRM-ILIS) in these samples. The $P_{app}$ value [Qr/dt=cumulative amount in the receiver compartment versus time; A=area of the cell monolayer; C0=initial concentration of the dosing solution] is commonly used to determine the ability of a molecule to cross the BBB.

Greater than 20-fold higher transcytosis of three co-administered antibodies FC5Fc, A20.1 and EG2. FC5 was found relative to negative controls which had low $P_{app}$ values (FIG. 8D).

Levels of IGF1R-3, IGF1R-4, and Fc-IGF1R5 measured in the bottom chamber at different time points are provided in FIG. 8E. All antibodies tested exhibited facilitated RMT in the AF-iPSC-BEC BBB model.

Figure 9:
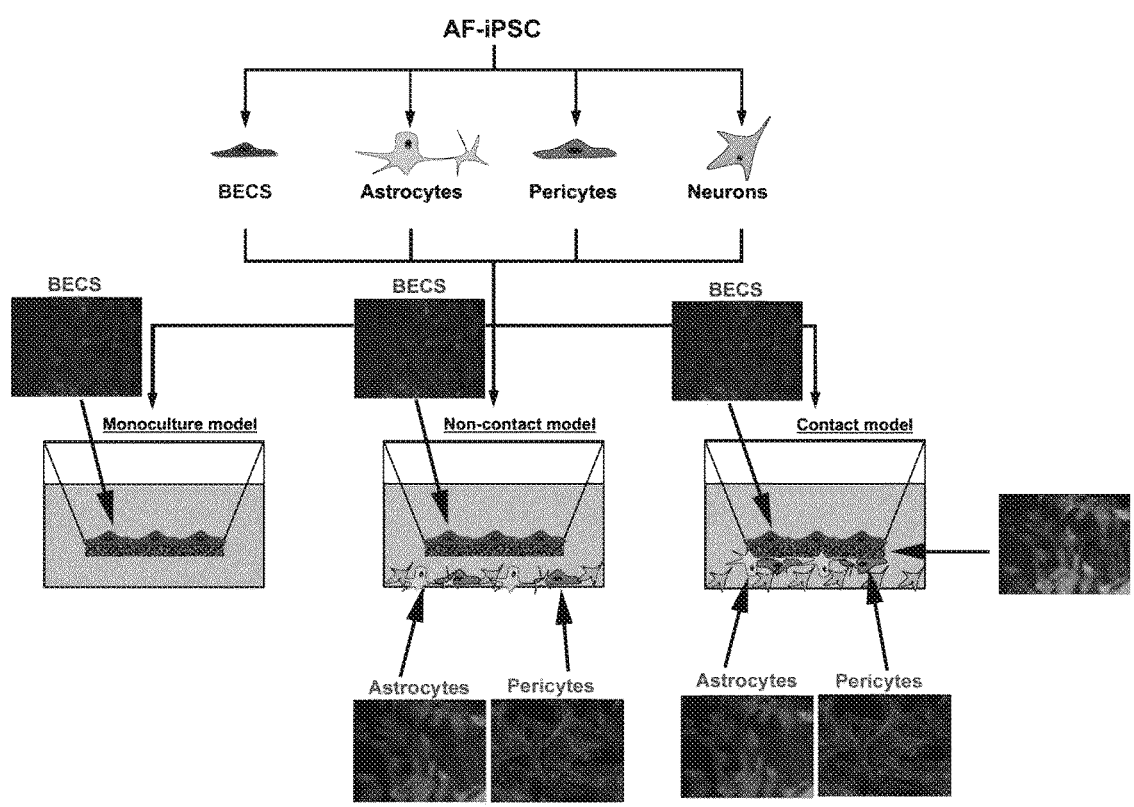
FIG. 9 is a schematic depicting generation of various BBB models comprising AF-iPSC-BECs as mono-culture or co-cultured with isogenic or allogenic astrocytes, pericytes and/or neurons, using a non-contact or contact model.
Figure 10:
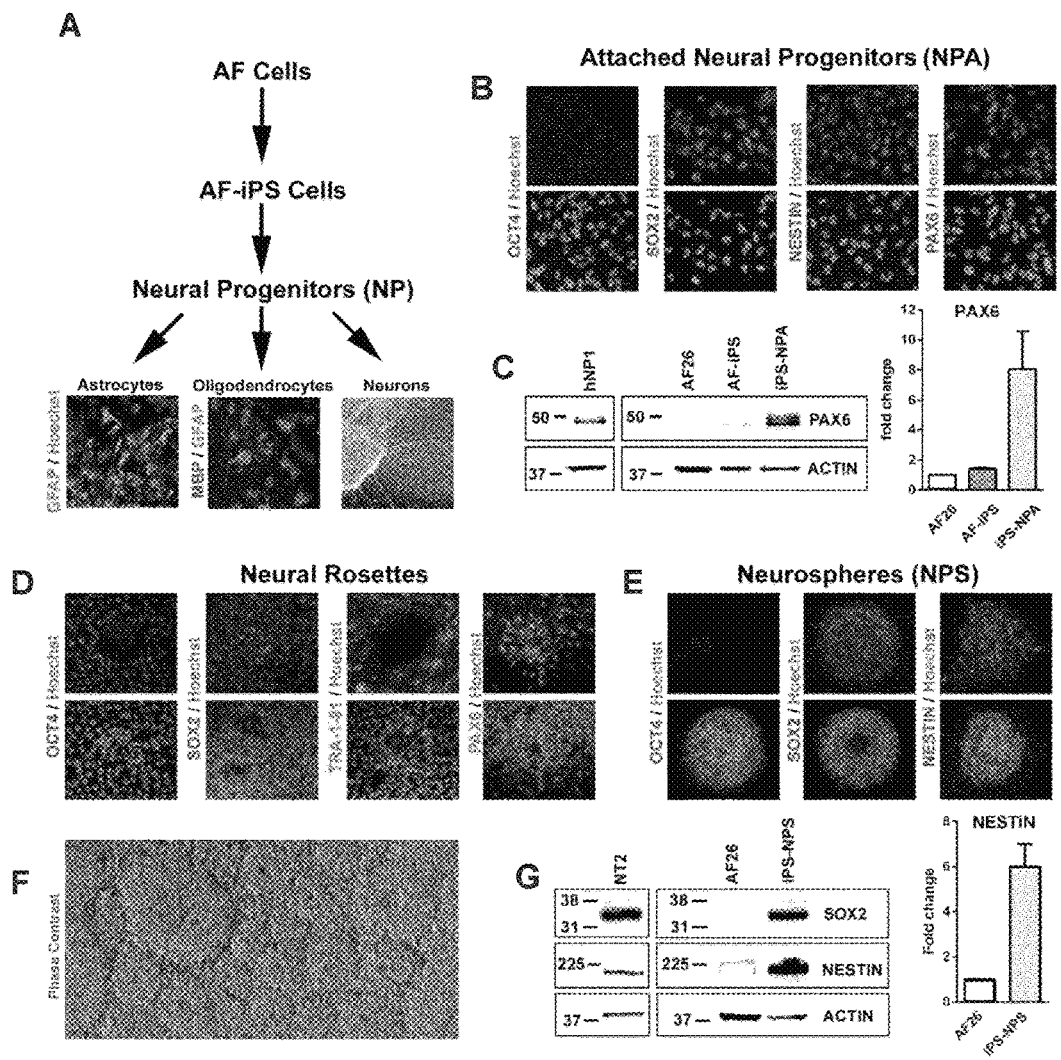
FIGS. 10A-G depict characterization of other CNS cell types generated from AF-iPSCs.

Example 5: Differentiation of hAF-iPSCs into Neural Progenitor Cells (NPs), Astrocytes, Oligodendrocytes and Neurons The inventors considered that it might be advantageous to generate isogenic or allogenic astrocytes, pericytes and/or neurons for use with the AF-iPSC-BEC BBB provided herein (FIG. 10A). A schematic depicting the process of generating various BBB models comprising AF-iPSC-BECs as mono-culture or co-cultured with isogenic or allogenic astrocytes, pericytes and/or neurons, using the non-contact or contact model, is shown in FIG. 9. Such isogenic cells might also be used as target cells in a method comprising testing permeability characteristics of a test agent with respect to the BBB.

6-well plates were coated with Matrigel hESC quality at least one hour prior to the start of experiments. DMEM/F12, Neural Induction Medium, and Accutase were pre-warmed to room temperature. Y27632 Stemolecule was added to the Neural Induction Medium to a final concentration of 10 μM to increase survival of single cells.

Maintenance medium was removed from well comprising ~80% confluent colonies of hAF-iPSCs and the cells were rinsed once with 2 mL of DMEM/F12. The medium was removed and Gentle cell dissociation buffer (1 mL/well of a 6-well plate) was added. The plate was incubated at room temperature or at 37° C. for about 5 minutes. Cell dissociation was monitored under a microscope. Cells were collected in a 15-mL tube, the well was rinsed with DMEM/F12, and medium collected in the same tube. The tube was centrifuged for 5 min at 200 g at room temperature. The supernatant was removed and the cells re-suspended in 4-5 mL of Stemdiff Neural Induction Medium. Cells were replated at 1:6 (vol/vol) ratio on Matrigel-coated plates in Stemdiff Neural Induction medium (Stem Cell Technology) and incubated. The next day, medium was removed and Neural Induction medium was added without Y27632 Stemolecule. The medium was replaced every other day. hiPSC were maintained in Stemdiff Neural Induction Medium for 15 days and at least 3 passages. After 3-4 days, the cultures were confluent (>70%). Confluent cells were passaged as described above. Stemdiff Neural induction medium was replaced every other day and NPs were passaged with Accutase every 5-7 days.

Neural progenitor cells formed a morphologically homogenous confluent monolayer, though some rosette-like radial arrangements of cells were observed (FIG. 10F). Morphology changes were noticeable after day 4, and neural morphology was obvious after 2 weeks of growth in Stemdiff Neural Induction medium. After about 3 weeks of growth in Stemdiff Neural Induction medium, the cells were passaged as above but the cells were seeded in Stemdiff Neural Progenitor medium (Stem Cell Technology) with 10 μM Y27632 Stemolecule. Samples were collected and immunocytochemistry, flow cytometry and/or RT-PCR were performed to confirm loss of pluripotent gene expression, such as OCT4, Nanog, TRA1-81, SSEA4, and to confirm expression of SOX2 and PAX6 (FIGS. 10B-E and G). Corresponding hiPSCs were used as a negative control.

Differentiation of hAF-IPSC-Derived Neural Progenitor Cells into Oligodendrocytes:

Medium was removed from the well of a 6-well plate and the well washed with DMEM/F12. DMEM/F12 was removed and 1 mL/well of Accutase was added to the cells. Cells were incubated for 2-5 minutes at 37° C., until individual single cells started to round up. Cell dissociation was monitored under the microscope. The cell suspension was collected in a 15 mL conical tube, the plate rinsed with a few mL of DMEM/F12 medium, and the medium transferred to the same conical tube. The cell suspension was centrifuged at 200 g for 3-5 minutes. The pellet was re-suspended in StemDiff Neural Progenitor medium. Cells were plated at a ratio 1: 6 in PLO/laminin (20 μg/mLPLO and 10 pg/mL laminin) plates and/or coated coverslips and incubated. On days 2-7, the medium provided to cells was Oligodendrocytes induction medium (DMEM-F12 with Glutamax, supplemented with 1% FBS, 100 ng/mL Sonic hedgehog (SHH)). On days 8-14, the medium provided to cells was Oligodendrocytes differentiation medium (DMEM-F12 with Glutamax, 1% FBS, 50 ng/mL PDGF, 50 ng/mL IGF). Cells were collected at day 8 and day 14 for Western blotting, RT-PCR and immunostaining (Olig2 and MBP).

Differentiation of hAF-IPSC-Derived Neural Progenitor Cells into Astrocytes:

Medium was removed from the well of a 6-well plate comprising AF-iPSC-derived neural progenitor cells and the well was washed with DMEM/F12. DMEM/F12 was removed and 1 mL/well of Accutase was added to the cells. Cells were incubated for 2-5 minutes at 37° C., until single cells started to round up. Cell dissociation was monitored under the microscope. The cell suspension was collected in a 15 mL conical tube, the plate rinsed with a few mL of DMEM/F12 medium, and the medium transferred to the same conical tube. The cell suspension was centrifuged at 200 g for 3-5 minutes. The pellet was re-suspended in StemDiff Neural Progenitor medium. Cells were plated at a ratio 1:6 in PLO/laminin (20 μg/mLPLO and 10 μg/mL laminin) plates and/or coated coverslips and incubated. On Day 2-4, the medium provided to cells was Astrocytes induction medium (DMEM-F12 with Glutamax, 5% FBS, 20 ng/mL EGF). On Days 5-7, the medium provided to cells was Astrocytes induction medium supplemented with 10 ng/mL CNTF. On Day 8-14, the medium was switched to Astrocytes Maintenance medium (DMEM-F12 with Glutamax, 1% FBS, 10 ng/mL CNTF) and changed every other day. Cells were collected after day 14 for Western blotting, RT-PCR and immunostaining (GFAP).

Dissociation of iPSC Colonies NPa (Neural Progenitors Attached), Producing NPf (Floating Neurospheres):

Medium from the well of a 6-well plate was removed and the well washed with DMEM/F12 (Life Technologies). DMEM/F12 was removed and 1 mL/well of Accutase (Stem Cell Technology) was added to the cells. Cells were incubated for 2-5 minutes at 37° C., until single cells started to round up. Cell dissociation was monitored under the microscope. The cell suspension was collected in a 15 mL conical tube, the plate rinsed with a few mL of DMEM/F12 medium, and the medium transferred to the same conical tube. The cell suspension was centrifuged at 200 g for 3-5 minutes. Supernatant was removed and the cells re-suspended in NPMM medium (Lonza). Cells were plated in Petri dishes for sphere formation or in Matrigel-coated 24 well plates for adherent cultures and incubated.

Dissociation of Neurospheres (NPf):

Spheres were collected in a 15 mL conical tube and allowed to sink for 3-5 minutes. Most of the medium was removed from the tube, and 5 mL DME/F12 was added. Spheres were allowed to sink for 3-5 min and the DME/F12 was removed. 1 mL of Accutase was added and incubated for 5 minutes at 37° C. The mixture was gently pipetted up and down until spheres appeared as smaller aggregates. ~200 µl of the pipetted mixture was placed in a well of a 24 well plate. Aggregate size was determined under the microscope. A total of 5 mL of NPMM medium was added to the sphere suspension. The tube containing the cell suspension was centrifuged at 200 g for 3-5 minutes at RT. Supernatant was removed and NPMM medium was added to the pellet, then plated in 100 mm Petri dishes and incubated. Medium was replaced every other day. A 40 µm strainer was placed in a 50 mL Falcon tube. The medium containing the spheres was applied to the reservoir of the strainer. The spheres were recovered from the strainer's filter by inverting the strainer in a 10 cm Petri dish and flushing the spheres with pre-warmed NPMM medium. NPMM medium was added to a total volume of 10 mL. The dish was incubated.

To start neuronal differentiation of attached neural progenitors, the medium was removed from the well of a 6-well plate and the well was washed with DMEM/F12. DMEM/F12 was removed and 1 mL/well of Accutase was added to the cells. Cells were incubated for 2-5 minutes at 37° C., until individual single cells started to round up. The spheres were collected in two 15 mL conical tubes. Up to 12 mL DMEM/F12 supplemented with B27 (Life Technologies) was added in one tube and/or N2 (Life Technologies) in the second. Spheres were transferred to Matrigel or Poly-lysine (PLL) coated wells of two 12 well plates with or without coverslips and incubated. Medium was replaced every other day. After day 1, spheres attached to the plate and started showing growth of neurites. Samples were collected at different times for immunostaining, Western blots and RT-PCR analysis. Electrophysiology was performed with neurons grown on PLL coated coverslips in DMEM/F12 supplemented with B27.

Figure 11:
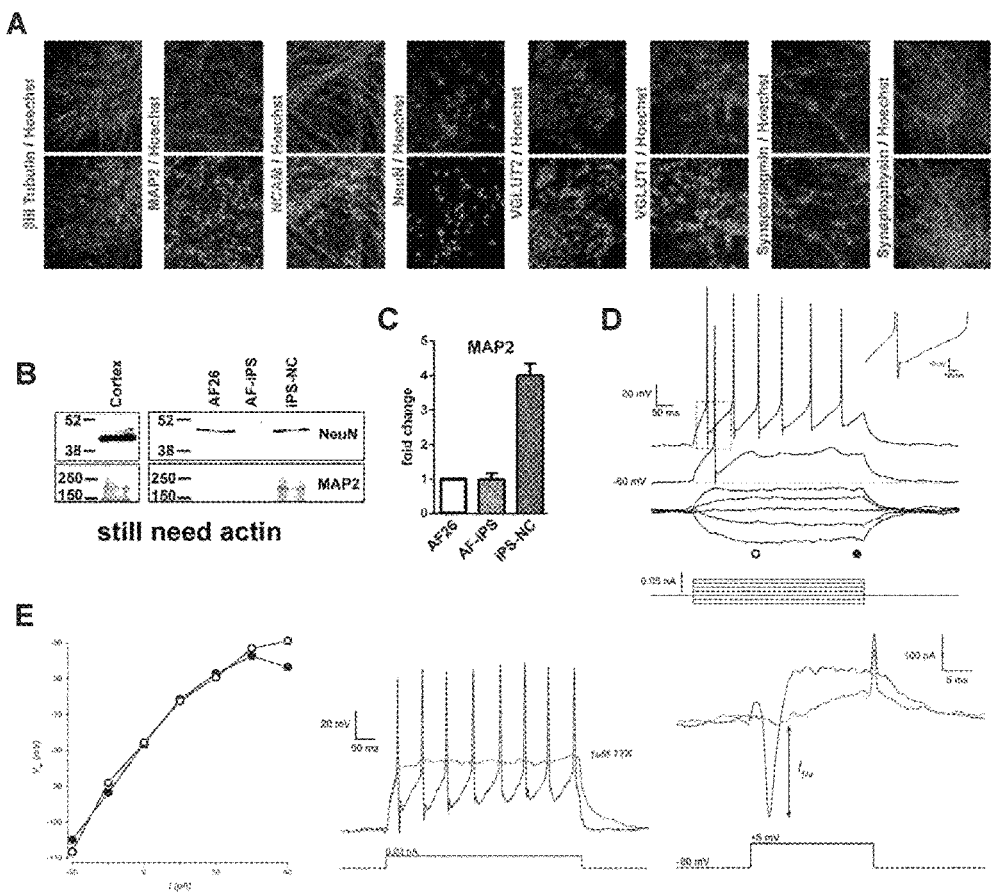
FIGS. 11A-E illustrate characterization of AF-iPSC-derived neurons.

Functional characterization of AF-iPSC-derived neurons was carried out using immunocytochemistry using a wide range of neuronal markers (FIG. 11A). Western blot confirmed the expression of NeuN and MAP2 in AF-iPSC-derived neuronal cells (iPS-NC) vs. control amniotic fluid cells (AF26) and AF-iPS cells (FIG. 11B). Voltage-clamp recording measurements confirmed function of AF-iPSC-BEC-derived neuron (FIG. 11C). The AF-iPSC-derived neurons showed tetrodotoxin (TTX)-sensitive spiking activity, using the whole-cell patch-clamp technique (FIG. 11D). Voltage response to a series of current pulses was also analyzed: current-voltage relationship at 500 ms (open circles) and 800 ms (filled circles) after onset of current pulses (FIG. 11E). Application of 1 µM TTX eliminated spiking activity.

Use of AF-iPSC-BEC BBBs in Drug Development

Figure 12:
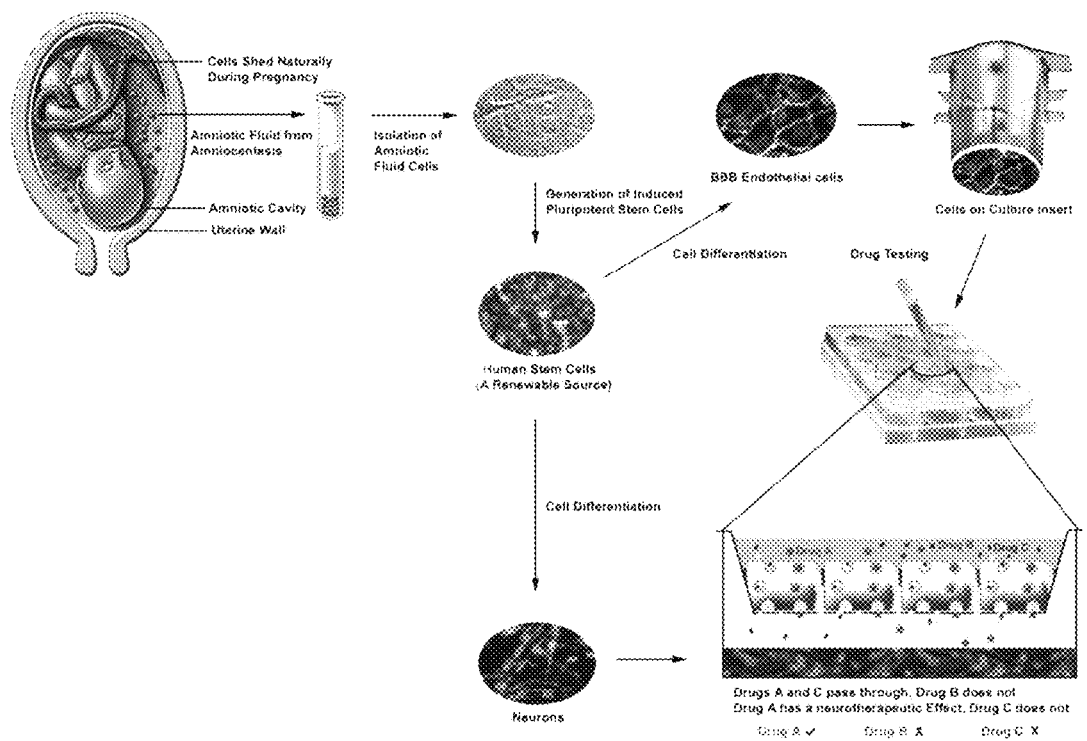
FIGS. 12 G-L depict Hoechst staining (blue) confirming the morphological changes in glutamate-treated (FIGS. 12J-L) versus control (FIGS. 12G-I) cultures. Phase contrast images have been shown without (FIGS. A, D, G and J) and in combination with Hoechst (FIGS. 12C, F, I and L).
Figure 12:
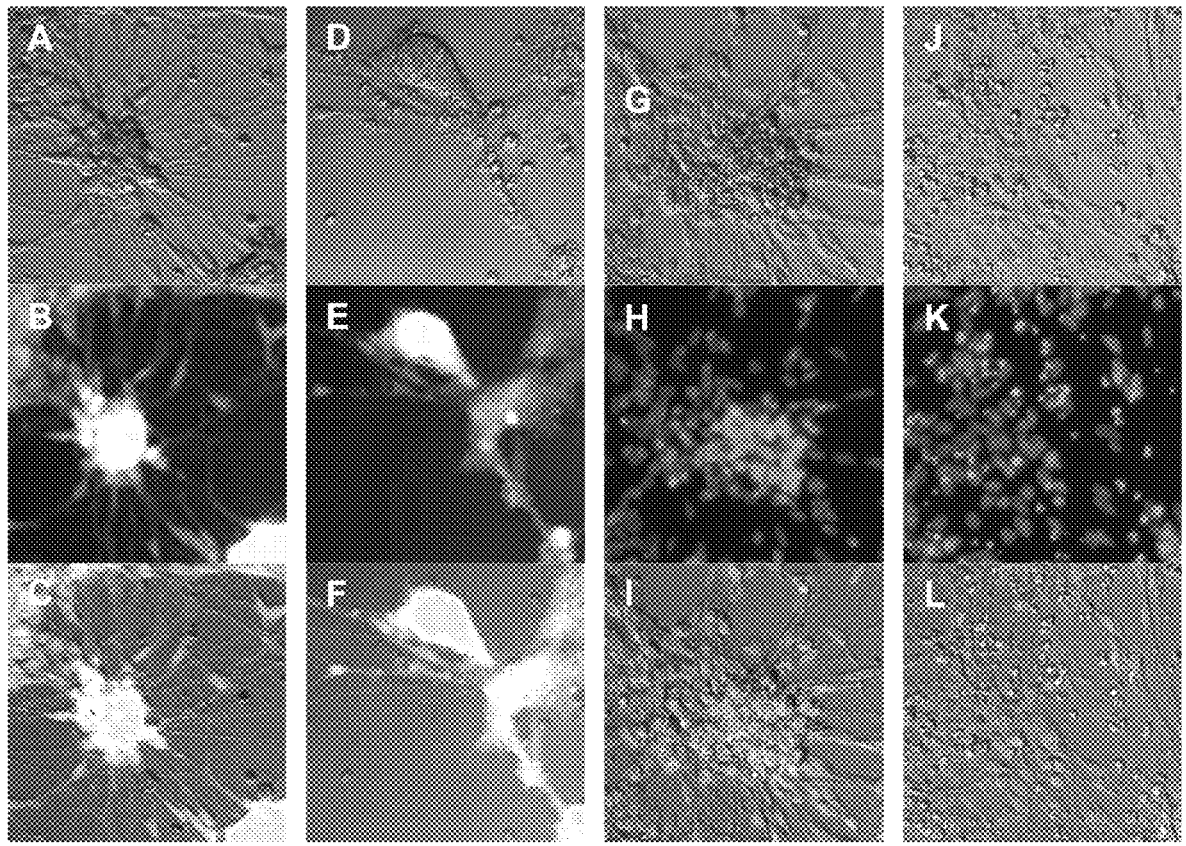

It is contemplated herein that the AF-iPSC-BEC BBB provided herein may suitable for various aspects of drug development (FIG. 12, upper panel). For example, AF-iPSC-BECs provided in a transwell BBB model may be used to assess the permeability of drug candidates and optionally to assess the function of BBB-permeable drug candidates on isogenic AF-iPSC-derived neurons (and/or other cell types) as their target. This feature of the BBB model provided herein allows a user to rank drug candidates based on their permeability through a human BBB model, followed by assessing their effects on target cells. These effects may include, for example, activation or inactivation of a signaling pathway, using a gene reporter system in the target cells or the therapeutic effects of drug candidates.

For example, cell survival/death can be assessed by CFDA staining/caspase glow in the neurons treated with a drug candidate penetrated through the BBB. For example, various neurotoxicity assays, using isogenic AF-iPSC-derived neurons may be carried out. Herein, the inventors have determined neuronal viability has by CFDA staining (green) in the absence (FIGS. 12A-C) or presence (FIGS. 12D-F) of glutamate for 6 hours in culture. A decrease in cell viability was observed in glutamate treated cultures (FIGS. 12D-F). This assay was complemented by Hoechst staining (blue, FIGS. 12G-L), further confirming the morphological changes in glutamate-treated (FIGS. 12J-L) versus control (FIGS. 12G-I) cultures.

Example 6: Immunofluorescence Assay

Alkaline Phosphatase Staining—Cells were grown in 12-well plate with Matrigel-coated 15 mm round coverslips. Culture medium was removed and cells were fixed for 1.5 minutes with 1 mL/well of 4% paraformaldehyde (PFA). PFA was removed and cells washed twice with 1×PBS by aspiration. Cells were incubated in the dark with staining solution (Fast Red Violet/Naphthol AS-BI phosphate solution/water in a 2:1:1 ratio) in 12-well plate for 15 minutes. Cells were washed once with PBS and photographed.

Immunolabeling—Cells were grown in 12-well plate with Matrigel-coated 15 mm round coverslips. Medium was removed and fixative added, 1 mL/well, for 8 minutes at room temperature. For most antigens, Genofix (DNAG-enotek) was used as fixative. For certain nuclear antigens, namely PAX6 and SOX17, PFA was the preferred fixative. Fixative was collected and replaced with 1 mL of PBS, then incubated for 5 minutes. Coverslips were washed two more times for at least 5 minutes with 1 mL of PBS. Cells were incubated with DAKO protein block, serum free (Product No. X090930-2) for 20 minutes at room temperature. Primary antibodies (see table below) were prepared. Coverslips were removed from 12-well plate, the back of the coverslip dried, and placed cell side up on parafilm in a humid chamber; 50 µL of antibody or PBS were immediately pipetted onto the coverslip and were incubated for 1 h at room temperature. Each coverslip was transferred cell side up into one well of a 12-well plate containing PBS. Coverslips were washed three times with PBS. Secondary antibodies were diluted according to the table below. 50 µL of secondary antibody was added per coverslip in humid chamber as described above for primary antibody. The humid chamber was covered with aluminum foil and incubated at room temperature for 1 h. Coverslips were washed three times with PBS. If labelling with more than one primary antibody was required, the above procedure was repeated for the second antibody. Coverslips were mounted onto slides, into a drop of DAKO fluorescent mounting medium spiked with 5 µg/mL of Hoechst 33258 to counterstain nuclei. Samples were viewed and photographed immediately, or stored at room temperature in the dark.

| Antibody/Reagent | Source | Dilution | Secondary Antibody |
| --- | --- | --- | --- |
| OCT4 | Mouse Monoclonal (Santa Cruz) | 1:100 | Rhodamine conjugated rabbit anti-mouse IgG |
| OCT4 | Rabbit Polyclonal (Abcam) | 1:100 | Rhodamine conjugated goat anti rabbit IgG (Invitrogen) |
| SOX2 | Rabbit Polyclonal | 1:5000 | Rhodamine conjugated goat anti rabbit IgG (Invitrogen) |
| NANOG | Goat Polyclonal (R&D Systems) | 1:100 | ALEXA568 conjugated rabbit anti goat IgG (Invitrogen) |
| TRA-1-81 | Mouse Monoclonal (Stemgent) | 1:100 | Directly conjugated to DyLight 488 |
| KLF4 | Rabbit Monoclonal (Abcam) | 1:500 | Rhodamine conjugated goat anti rabbit IgG (Invitrogen) |
| SSEA3 | Rat Polyclonal (R&D Systems) | 1:20 | ALEXA488 goat conjugated anti rat IgG (Invitrogen) |
| SSEA4 | Mouse Monoclonal (R&D Systems) | 1:20 | Rhodamine conjugated rabbit anti mouse IgG |
| SMA | Mouse monoclonal (Sigma) | 1:100 | Rhodamine conjugated rabbit anti mouse IgG |
| CD30 | Mouse monoclonal (BD Biosciences) | 1:20 | Antibody directly conjugated to BV421 |
| Nestin | Rabbit Polyclonal (Millipore) | 1:200 | Rhodamine conjugated goat anti rabbit IgG (Invitrogen) |
| MAP2 | Mouse Monoclonal (Sigma) | 1:100 | Rhodamine conjugated rabbit anti mouse IgG |
| NCAM | Rabbit Polyclonal (Millipore) | 1:100 | ALEXA488 conjugated goat anti rabbit IgG (Invitrogen) |
| BIII-Tubulin | Mouse Monoclonal (Millipore) | 1:200 | Rhodamine conjugated rabbit anti mouse IgG |
| VGLUT1 | Mouse Monoclonal (Millipore) | 1:100 | Rhodamine conjugated rabbit anti mouse IgG |
| VGLUT2 | Mouse Monoclonal (Millipore) | 1:100 | Rhodamine conjugated rabbit anti mouse IgG |
| GFAP | Rabbit Polyclonal (DAKO) | 1:500 | ALEXA488 conjugated goat anti rabbit IgG (Invitrogen) |
| NeuN | Rabbit Polyclonal (Abcam) | 1:500 | Rhodamine conjugated goat anti rabbit IgG (Invitrogen) |
| Synaptophysin | Mouse Monoclonal (Sigma) | 1:200 | Rhodamine conjugated rabbit anti mouse IgG |
| Synaptotagmin | Mouse Monoclonal | 1:100 | Rhodamine conjugated rabbit anti mouse IgG |
| SOX17 | Goat Polyclonal (R&D Systems) | 1:100 | ALEXA568 conjugated rabbit anti goat IgG (Invitrogen) |
| MBP | Mouse Monoclonal (Millipore) | 1:1000 | Rhodamine conjugated rabbit anti mouse IgG |
| PAX6 | Rabbit Polyclonal (Cedarlane) | 1:50 | Rhodamine conjugated goat anti rabbit IgG (Invitrogen) |
| ZO-1 | Rabbit Polyclonal (Abcam) | 1:100 | Rhodamine conjugated goat anti rabbit IgG (Invitrogen) |
| Claudin 5 | Rabbit Polyclonal (Abcam) | 1:100 | Rhodamine conjugated goat anti rabbit IgG (Invitrogen) |
| VWF | Rabbit Polyclonal | 1:200 | Rhodamine conjugated goat anti rabbit IgG (Invitrogen) |
| CD31 | Rabbit Polyclonal (Abcam) | 1:20 | Rhodamine conjugated goat anti rabbit IgG (Invitrogen) |
| Occludin | Rabbit Polyclonal (Abcam) | 1:100 | Rhodamine conjugated goat anti rabbit IgG (Invitrogen) |
| Connexin 43 | Rabbit polyclonal (Abcam) | 1:500 | Rhodamine conjugated goat anti rabbit IgG (Invitrogen) |
| GLUT1 | Mouse Monoclonal (Abcam) | 1:100 | Rhodamine conjugated rabbit anti mouse IgG |
| Tomato lactin | (Vector labs) | 1:500 | Directly conjugated to FITC |
| ULEX | (Vector labs) | 1:500 | Directly conjugated to FITC |
| Troponin T ALEXA-Phalloidin | Mouse monoclonal | 1:1000 | Rhodamine conjugated rabbit anti mouse IgG |

All patents, patent applications and publications referred to herein and throughout the application are hereby incorporated by reference.

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference as if set forth in their entirety.

We claim:

1. A blood brain barrier model comprising:
   a permeable support having a surface comprising extracellular matrix proteins; and
   a plurality of human brain endothelial cells (hBECs), wherein the hBECs are derived from induced pluripotent stem cells made from amniotic fluid cells (AF-iPSC-BECs),
   wherein the plurality of hBECs express WNT7A, ZO-3, claudin-5, occludin, ZO-1 and GLUT-1 and express one or more of FZD7, WNT7B, APCDD1, and STRA6,
   wherein the hBECs are grown to confluence in a human endothelial serum free (EM) medium comprising 1% platelet-poor derived serum and 20 ng/ml human basic fibroblast growth factor (bFGF) on the permeable support,
   wherein the blood brain barrier model does not comprise co-cultured cells,
   wherein the hBECs are grown in the absence of retinoic acid, and
   wherein the plurality of hBECs have a trans-endothelial electrical resistance (TEER) of at least about 400 $\Omega \cdot cm^2$.

2. The blood brain barrier model of claim 1, wherein the plurality of hBECs express ABCG2, PGP and transferrin receptor.

3. The blood brain barrier model of claim 1, wherein the plurality of hBECs have a trans-endothelial electrical resistance (TEER) between about 400 and 700 $\Omega \cdot cm^2$.

4. The blood brain barrier model of claim 1, wherein the plurality of hBECs grown to confluence on the permeable support are provided within a liquid-containing vessel, thereby forming a barrier between a top and a bottom chamber of the vessel.

* * * * *